(12) United States Patent
Russell et al.

(10) Patent No.: US 7,862,570 B2
(45) Date of Patent: Jan. 4, 2011

(54) SURGICAL POSITIONERS

(75) Inventors: Thomas A. Russell, Collierville, TN (US); Lauralan Terrill-Grisoni, Cordova, TN (US); Patrick J. Culley, Memphis, TN (US); Therise Ruffin, Collierville, TN (US); Kevin Raburn, Memphis, TN (US)

(73) Assignee: Smith & Nephew, Inc., Memphis, TN (US), part interest ( * ) Notice: Subject to any disclaimer, the term of this patent is extended or adjusted under 35 U.S.C. 154(b) by 1635 days.

(21) Appl. No.: 10/679,158

(22) Filed: Oct. 3, 2003

(65) Prior Publication Data

US 2005/0075632 A1   Apr. 7, 2005

(51) Int. Cl.
*A61F 5/00* (2006.01)
(52) U.S. Cl. .................. 606/87; 606/130; 600/424
(58) Field of Classification Search .............. 600/407, 600/414, 417, 426, 429; 606/130, 87
See application file for complete search history.

(56) References Cited

U.S. PATENT DOCUMENTS

| | | |
|---|---|---|
| 100,602 A | 3/1870 | Coes |
| 1,076,971 A | 10/1913 | Geiger |
| 1,201,467 A | 10/1916 | Hoglund |
| 2,092,869 A | 9/1937 | Baum |
| 3,412,733 A | 11/1968 | Ross |
| 3,457,922 A | 7/1969 | Ray |
| 3,702,611 A | 11/1972 | Fishbein |
| 4,305,394 A | 12/1981 | Bertuch, Jr. |
| 4,323,080 A | 4/1982 | Melharty |
| 4,421,112 A | 12/1983 | Mains et al. |
| 4,456,010 A | 6/1984 | Reimels et al. |
| 4,457,307 A | 7/1984 | Stillwell |
| 4,483,554 A | 11/1984 | Ernst |
| 4,524,766 A | 6/1985 | Petersen |
| 4,534,364 A | 8/1985 | Lamoreux |
| 4,565,192 A | 1/1986 | Shapiro |
| 4,566,448 A | 1/1986 | Rohr, Jr. |

(Continued)

FOREIGN PATENT DOCUMENTS

DE    42 25 112 C    12/1993

(Continued)

OTHER PUBLICATIONS

DePuy, a Johnson & Johnson Company, Brochure entitled 'S-ROM Modular Hip System Minimally Invasive Calcar Miller Surgical Technique,' 12 pages (2004).

(Continued)

*Primary Examiner*—Brian Casler
*Assistant Examiner*—Baisakhi Roy
(74) *Attorney, Agent, or Firm*—Kilpatrick Stockton LLP

(57) ABSTRACT

Surgical positioners may include platforms, surgical item positioners and/or surgical references as well as methods for using stabilizer platforms, surgical item positioners and/or surgical references. Stabilizer platforms may include low profile platforms rigidly mounted to portions of an individual's anatomy. Various items may be secured and/or stabilized by the stabilizer platform, including support platforms as well as surgical references. Support platforms may stabilize and assist surgeons in using, navigating, aligning and positioning surgical items. Surgical references may include modular fiducial systems that may be secured to stabilizer platforms, support platforms, surgical items and/or directly to portions of an individual's anatomy.

34 Claims, 14 Drawing Sheets

U.S. PATENT DOCUMENTS

| | | | |
|---|---|---|---|
| 4,567,885 A | 2/1986 | Androphy | |
| 4,567,886 A | 2/1986 | Petersen | |
| 4,574,794 A | 3/1986 | Cooke et al. | |
| 4,583,554 A | 4/1986 | Mittelman et al. | |
| 4,671,275 A | 6/1987 | Deyerle | |
| 4,703,751 A | 11/1987 | Pohl | |
| 4,712,951 A | 12/1987 | Brown | |
| 4,718,413 A | 1/1988 | Johnson | |
| 4,722,056 A | 1/1988 | Roberts et al. | |
| 4,738,256 A | 4/1988 | Freeman et al. | |
| 4,759,350 A | 7/1988 | Dunn et al. | |
| 4,768,504 A | 9/1988 | Ender | |
| 4,777,942 A | 10/1988 | Frey et al. | |
| 4,802,468 A | 2/1989 | Powlan | |
| 4,803,976 A | 2/1989 | Frigg et al. | |
| 4,809,689 A | 3/1989 | Anapliotis | |
| 4,815,899 A | 3/1989 | Regan | |
| 4,875,475 A | 10/1989 | Comte et al. | |
| 4,892,093 A | 1/1990 | Zarnowski et al. | |
| 4,913,163 A | 4/1990 | Roger et al. | |
| 4,938,762 A | 7/1990 | Wehrli | |
| 4,952,213 A | 8/1990 | Bowman et al. | |
| 4,964,862 A | 10/1990 | Arms | |
| 4,991,579 A | 2/1991 | Allen | |
| 5,002,545 A | 3/1991 | Whiteside et al. | |
| 5,002,578 A | 3/1991 | Luman | |
| 5,016,639 A | 5/1991 | Allen | |
| 5,037,423 A | 8/1991 | Kenna | |
| 5,037,426 A | 8/1991 | Goble et al. | |
| 5,049,149 A | 9/1991 | Schmidt | |
| 5,053,039 A | 10/1991 | Hofmann et al. | |
| 5,078,719 A | 1/1992 | Schreiber | |
| 5,092,869 A | 3/1992 | Waldron | |
| 5,094,241 A | 3/1992 | Allen | |
| 5,097,839 A | 3/1992 | Allen | |
| 5,098,426 A | 3/1992 | Sklar et al. | |
| 5,116,338 A | 5/1992 | Poggie et al. | |
| 5,119,817 A | 6/1992 | Allen | |
| 5,122,144 A | 6/1992 | Bert et al. | |
| 5,129,909 A | 7/1992 | Sutherland | |
| 5,147,408 A | 9/1992 | Noble | |
| 5,190,547 A | 3/1993 | Barber, Jr. et al. | |
| 5,211,164 A | 5/1993 | Allen | |
| 5,213,312 A | 5/1993 | MacDonald | |
| 5,217,499 A | 6/1993 | Shelley | |
| 5,230,338 A | 7/1993 | Allen et al. | |
| 5,246,444 A | 9/1993 | Schreiber | |
| 5,254,119 A | 10/1993 | Schreiber | |
| 5,263,972 A | 11/1993 | Evans et al. | |
| 5,289,826 A | 3/1994 | Kovacevic | |
| 5,305,203 A | 4/1994 | Raab | |
| 5,342,366 A | 8/1994 | Whiteside et al. | |
| 5,342,368 A | 8/1994 | Petersen | |
| 5,360,016 A | 11/1994 | Kovacevic | |
| 5,364,401 A | 11/1994 | Ferrante et al. | |
| 5,364,402 A | 11/1994 | Mumme et al. | |
| 5,365,996 A | 11/1994 | Crook | |
| 5,375,588 A | 12/1994 | Yoon | |
| 5,379,133 A | 1/1995 | Kirk | |
| 5,383,454 A | 1/1995 | Bucholz | |
| 5,387,218 A | 2/1995 | Meswania et al. | |
| 5,389,101 A | 2/1995 | Heilbrun et al. | |
| 5,395,376 A | 3/1995 | Caspari et al. | |
| 5,397,329 A | 3/1995 | Allen | |
| 5,403,320 A | 4/1995 | Luman | |
| 5,423,828 A | 6/1995 | Benson | |
| 5,425,355 A | 6/1995 | Kulick | |
| 5,445,166 A | 8/1995 | Taylor | |
| 5,445,642 A | 8/1995 | McNulty et al. | |
| 5,449,360 A | 9/1995 | Schreiber | |
| 5,452,407 A | 9/1995 | Crook | |
| 5,462,548 A | 10/1995 | Pappas et al. | |
| 5,462,549 A | 10/1995 | Glock | |
| 5,468,244 A | 11/1995 | Attfield et al. | |
| 5,470,354 A | 11/1995 | Hershberger et al. | |
| 5,474,559 A | 12/1995 | Bertin et al. | |
| 5,484,437 A | 1/1996 | Michelson | |
| 5,486,178 A | 1/1996 | Hodge | |
| 5,490,854 A | 2/1996 | Fisher et al. | |
| 5,491,510 A | 2/1996 | Gove | |
| 5,507,824 A | 4/1996 | Lennox | |
| 5,514,139 A | 5/1996 | Goldstein et al. | |
| 5,517,990 A | 5/1996 | Kalfas et al. | |
| 5,527,316 A | 6/1996 | Williamson | |
| 5,540,691 A | 7/1996 | Elmstrom et al. | |
| 5,540,694 A | 7/1996 | DeCarlo, Jr. | |
| 5,540,695 A | 7/1996 | Levy | |
| 5,540,696 A | 7/1996 | Booth, Jr. et al. | |
| 5,569,260 A | 10/1996 | Petersen | |
| 5,597,379 A | 1/1997 | Haines et al. | |
| 5,598,269 A | 1/1997 | Kitaevich et al. | |
| 5,603,318 A | 2/1997 | Heilbrun et al. | |
| 5,613,969 A | 3/1997 | Jenkins, Jr. | |
| 5,643,268 A | 7/1997 | Vilsmeier et al. | |
| 5,643,272 A | 7/1997 | Haines et al. | |
| 5,658,290 A | 8/1997 | Lechot | |
| 5,669,914 A | 9/1997 | Eckhoff | |
| 5,676,668 A | 10/1997 | McCue et al. | |
| 5,681,316 A | 10/1997 | DeOrio et al. | |
| 5,682,886 A | 11/1997 | Delp et al. | |
| 5,683,397 A | 11/1997 | Vendrely et al. | |
| 5,688,279 A | 11/1997 | McNulty et al. | |
| 5,693,056 A | 12/1997 | Carls et al. | |
| 5,695,501 A | 12/1997 | Carol et al. | |
| 5,702,406 A | 12/1997 | Vilsmeier et al. | |
| 5,704,941 A | 1/1998 | Jacober et al. | |
| 5,707,370 A | 1/1998 | Berki et al. | |
| 5,709,689 A | 1/1998 | Ferrante et al. | |
| 5,715,836 A | 2/1998 | Kliegis et al. | |
| 5,716,361 A | 2/1998 | Masini | |
| 5,720,752 A | 2/1998 | Elliott et al. | |
| 5,722,978 A | 3/1998 | Jenkins, Jr. | |
| 5,733,292 A | 3/1998 | Gustilo et al. | |
| 5,735,904 A | 4/1998 | Pappas | |
| 5,743,915 A | 4/1998 | Bertin et al. | |
| 5,748,767 A | 5/1998 | Raab | |
| 5,755,725 A | 5/1998 | Druais | |
| 5,755,803 A | 5/1998 | Haines et al. | |
| 5,768,134 A | 6/1998 | Swaelens et al. | |
| 5,769,861 A | 6/1998 | Vilsmeier | |
| 5,772,593 A | 6/1998 | Hakamata | |
| 5,772,594 A | 6/1998 | Barrick | |
| 5,776,064 A | 7/1998 | Kalfas et al. | |
| 5,782,842 A | 7/1998 | Kloess et al. | |
| 5,792,147 A | 8/1998 | Evans et al. | |
| 5,797,924 A | 8/1998 | Schulte et al. | |
| 5,799,055 A | 8/1998 | Peshkin et al. | |
| 5,800,352 A | 9/1998 | Ferre et al. | |
| 5,800,438 A | 9/1998 | Tuke et al. | |
| 5,807,252 A | 9/1998 | Hassfeld et al. | |
| 5,810,827 A | 9/1998 | Haines et al. | |
| 5,810,841 A | 9/1998 | McNeirney et al. | |
| 5,817,097 A | 10/1998 | Howard et al. | |
| 5,830,214 A | 11/1998 | Flom et al. | |
| 5,836,954 A | 11/1998 | Heilbrun et al. | |
| 5,848,967 A | 12/1998 | Cosman | |
| 5,850,836 A | 12/1998 | Steiger et al. | |
| 5,860,981 A | 1/1999 | Bertin et al. | |
| 5,865,809 A | 2/1999 | Moenning et al. | |
| 5,871,018 A | 2/1999 | Delp et al. | |
| 5,871,445 A | 2/1999 | Bucholz | |
| 5,879,352 A | 3/1999 | Filoso et al. | |
| 5,879,354 A | 3/1999 | Haines et al. | |
| 5,880,976 A | 3/1999 | DiGioia III et al. | |

| Patent | Date | Inventor |
|---|---|---|
| 5,885,296 A | 3/1999 | Masini |
| 5,885,297 A | 3/1999 | Matsen, III |
| 5,897,559 A | 4/1999 | Masinie |
| 5,916,221 A | 6/1999 | Hodorek et al. |
| 5,920,395 A | 7/1999 | Schulz |
| 5,921,992 A | 7/1999 | Costales et al. |
| 5,925,049 A | 7/1999 | Gustilo et al. |
| 5,935,128 A | 8/1999 | Carter et al. |
| 5,938,665 A | 8/1999 | Martin |
| 5,944,722 A | 8/1999 | Masini |
| 5,947,971 A | 9/1999 | Kuslich et al. |
| 5,947,973 A | 9/1999 | Masini |
| 5,951,561 A | 9/1999 | Pepper et al. |
| 5,957,926 A | 9/1999 | Masini |
| 5,961,523 A | 10/1999 | Masini |
| 5,971,989 A | 10/1999 | Masini |
| 5,980,526 A | 11/1999 | Johnson et al. |
| 5,980,535 A | 11/1999 | Barnett et al. |
| 5,999,837 A | 12/1999 | Messner et al. |
| 6,001,106 A | 12/1999 | Ryan et al. |
| 6,002,859 A | 12/1999 | DiGioia, III et al. |
| 6,006,126 A | 12/1999 | Cosman |
| 6,007,537 A | 12/1999 | Burkinshaw et al. |
| 6,010,506 A | 1/2000 | Gosney et al. |
| 6,011,987 A | 1/2000 | Barnett |
| 6,016,606 A | 1/2000 | Oliver et al. |
| 6,021,342 A | 2/2000 | Brabrand |
| 6,021,343 A | 2/2000 | Foley et al. |
| 6,022,377 A | 2/2000 | Nuelle et al. |
| 6,026,315 A | 2/2000 | Lenz et al. |
| 6,030,391 A | 2/2000 | Brainard et al. |
| 6,033,410 A | 3/2000 | McLean et al. |
| 6,041,249 A | 3/2000 | Regn |
| 6,044,291 A | 3/2000 | Rockseisen |
| 6,045,556 A | 4/2000 | Cohen |
| 6,050,724 A | 4/2000 | Schmitz et al. |
| 6,053,922 A | 4/2000 | Krause et al. |
| 6,056,756 A | 5/2000 | Eng et al. |
| 6,068,633 A | 5/2000 | Masini |
| 6,069,932 A | 5/2000 | Oeshkin et al. |
| 6,073,044 A | 6/2000 | Fitzpatrick et al. |
| 6,077,269 A | 6/2000 | Masini |
| 6,081,336 A | 6/2000 | Messner et al. |
| 6,083,163 A | 7/2000 | Wegner et al. |
| 6,096,048 A | 8/2000 | Howard et al. |
| 6,102,916 A | 8/2000 | Masini |
| 6,132,433 A | 10/2000 | Whelan |
| 6,143,390 A | 11/2000 | Takamiya et al. |
| 6,144,875 A | 11/2000 | Schweikard et al. |
| 6,146,390 A | 11/2000 | Heilbrun et al. |
| 6,148,280 A | 11/2000 | Kramer |
| 6,161,033 A | 12/2000 | Kuhn |
| 6,162,190 A | 12/2000 | Kramer |
| 6,165,181 A | 12/2000 | Heilbrun et al. |
| 6,167,145 A | 12/2000 | Foley et al. |
| 6,167,292 A | 12/2000 | Badano et al. |
| 6,167,295 A | 12/2000 | Cosman |
| 6,167,296 A | 12/2000 | Shahidi |
| 6,168,627 B1 | 1/2001 | Huebner |
| 6,174,335 B1 | 1/2001 | Varieur |
| 6,185,315 B1 | 2/2001 | Schmucker et al. |
| 6,187,010 B1 | 2/2001 | Masini |
| 6,190,320 B1 | 2/2001 | Lelong |
| 6,190,395 B1 | 2/2001 | Williams |
| 6,195,168 B1 | 2/2001 | De Lega et al. |
| 6,197,064 B1 | 3/2001 | Haines et al. |
| 6,198,794 B1 | 3/2001 | Peshkin et al. |
| 6,200,316 B1 | 3/2001 | Zwirkoski et al. |
| 6,205,411 B1 | 3/2001 | DiGioia, III et al. |
| 6,211,976 B1 | 4/2001 | Popovich et al. |
| 6,214,011 B1 | 4/2001 | Masini |
| 6,216,029 B1 | 4/2001 | Paltieli |
| 6,223,067 B1 | 4/2001 | Vilsmeier et al. |
| 6,226,548 B1 | 5/2001 | Foley et al. |
| 6,228,090 B1 | 5/2001 | Waddell |
| 6,228,092 B1 | 5/2001 | Mikhail |
| 6,235,038 B1 | 5/2001 | Hunter et al. |
| 6,236,875 B1 | 5/2001 | Bucholz et al. |
| 6,241,735 B1 | 6/2001 | Marmulla |
| 6,249,581 B1 | 6/2001 | Kok |
| 6,258,095 B1 | 7/2001 | Lombardo et al. |
| 6,258,096 B1 | 7/2001 | Seki |
| 6,264,647 B1 | 7/2001 | Lechot |
| 6,283,971 B1 | 9/2001 | Temeles |
| 6,285,902 B1 | 9/2001 | Kienzle, III et al. |
| 6,295,513 B1 | 9/2001 | Thackston |
| 6,317,616 B1 | 11/2001 | Glossop |
| 6,319,256 B1 | 11/2001 | Spotorno |
| 6,332,891 B1 | 12/2001 | Himes |
| 6,333,971 B2 | 12/2001 | McCrory et al. |
| 6,344,853 B1 | 2/2002 | Knight |
| 6,347,240 B1 | 2/2002 | Foley et al. |
| 6,351,659 B1 | 2/2002 | Vilsmeier |
| 6,351,661 B1 | 2/2002 | Cosman |
| 6,377,839 B1 | 4/2002 | Kalfas et al. |
| 6,381,485 B1 | 4/2002 | Hunter et al. |
| 6,383,188 B2 | 5/2002 | Kuslich et al. |
| 6,385,475 B1 | 5/2002 | Cinquin et al. |
| 6,405,072 B1 | 6/2002 | Cosman |
| 6,413,261 B1 | 7/2002 | Grundei |
| 6,434,507 B1 | 8/2002 | Clayton et al. |
| 6,440,140 B2 | 8/2002 | Bullivant et al. |
| 6,443,956 B1 | 9/2002 | Ray |
| 6,451,059 B1 | 9/2002 | Janas et al. |
| 6,458,135 B1 | 10/2002 | Harwin et al. |
| 6,463,351 B1 | 10/2002 | Clynch |
| 6,468,202 B1 | 10/2002 | Irion et al. |
| 6,477,400 B1 | 11/2002 | Barrick |
| 6,478,799 B1 | 11/2002 | Williamson |
| 6,490,467 B1 | 12/2002 | Bucholz et al. |
| 6,491,429 B1 | 12/2002 | Suhm |
| 6,491,702 B2 | 12/2002 | Heilbrun et al. |
| 6,503,249 B1 | 1/2003 | Krause |
| 6,503,254 B2 | 1/2003 | Masini |
| 6,527,443 B1 | 3/2003 | Vilsmeier et al. |
| 6,540,739 B2 | 4/2003 | Lechot |
| 6,546,279 B1 | 4/2003 | Bova et al. |
| 6,551,319 B2 | 4/2003 | Lieberman |
| 6,551,324 B2 | 4/2003 | Muller |
| 6,551,325 B2 | 4/2003 | Neubauer et al. |
| 6,554,837 B1 | 4/2003 | Hauri et al. |
| 6,558,391 B2 | 5/2003 | Axelson, Jr. et al. |
| 6,558,421 B1 | 5/2003 | Fell et al. |
| 6,567,687 B2 | 5/2003 | Front et al. |
| 6,574,493 B2 | 6/2003 | Rasche et al. |
| 6,595,997 B2 | 7/2003 | Axelson, Jr., et al. |
| 6,602,259 B1 | 8/2003 | Masini |
| 6,620,268 B2 | 9/2003 | Cho et al. |
| 6,620,168 B1 | 10/2003 | Lombardo et al. |
| 6,640,127 B1 | 10/2003 | Kosaka et al. |
| 6,652,142 B2 | 11/2003 | Launay et al. |
| 6,662,036 B2 | 12/2003 | Cosman |
| 6,673,077 B1 | 1/2004 | Katz |
| 6,675,040 B1 | 1/2004 | Cosman |
| 6,685,711 B2 | 2/2004 | Axelson, Jr. et al. |
| 6,690,964 B2 | 2/2004 | Bieger et al. |
| 6,692,447 B1 | 2/2004 | Picard |
| 6,695,848 B2 | 2/2004 | Haines |
| 6,702,821 B2 | 3/2004 | Bonutti |
| 6,711,431 B2 | 3/2004 | Sarin et al. |
| 6,712,823 B2 | 3/2004 | Grusin et al. |
| 6,712,824 B2 | 3/2004 | Millard et al. |
| 6,716,249 B2 | 4/2004 | Hyde |
| 6,718,194 B2 | 4/2004 | Kienzle, III |
| 6,725,082 B2 | 4/2004 | Sati et al. |
| 6,728,599 B2 | 4/2004 | Wang |

| | | |
|---|---|---|
| 6,738,657 B1 | 5/2004 | Franklin et al. |
| 6,772,026 B2 | 8/2004 | Bradbury et al. |
| 6,780,190 B2 | 8/2004 | Maroney |
| 6,785,593 B2 | 8/2004 | Wang |
| 6,799,088 B2 | 9/2004 | Wang |
| 6,814,490 B1 | 11/2004 | Suhm et al. |
| 6,827,723 B2 | 12/2004 | Carson |
| 6,836,703 B2 | 12/2004 | Wang |
| 6,871,117 B2 | 3/2005 | Wang |
| 6,882,982 B2 | 4/2005 | McMenimen |
| 6,892,112 B2 | 5/2005 | Wang |
| 6,905,514 B2 | 6/2005 | Carignan et al. |
| 6,923,617 B2 | 8/2005 | Carson |
| 6,947,786 B2 | 9/2005 | Simon et al. |
| 6,993,374 B2 | 1/2006 | Sasso |
| 7,001,346 B2 | 2/2006 | White |
| 7,035,702 B2 | 4/2006 | Jelonek et al. |
| 7,237,558 B2 | 7/2007 | Smothers |
| 7,241,298 B2 | 7/2007 | Nemec et al. |
| 7,468,075 B2 | 12/2008 | Lang et al. |
| 7,634,119 B2 | 12/2009 | Tsougarakis et al. |
| 2001/0001120 A1 | 5/2001 | Masini |
| 2001/0010004 A1 | 7/2001 | Traxel et al. |
| 2001/0014772 A1 | 8/2001 | Lampotang et al. |
| 2001/0016745 A1 | 8/2001 | Bullivant et al. |
| 2001/0034530 A1 | 10/2001 | Malackowski et al. |
| 2001/0036245 A1 | 11/2001 | Kienzle, III et al. |
| 2001/0039421 A1 | 11/2001 | Heilbrun et al. |
| 2002/0002330 A1 | 1/2002 | Vilsmeier |
| 2002/0002365 A1 | 1/2002 | Lechot |
| 2002/0007294 A1 | 1/2002 | Bradbury et al. |
| 2002/0011594 A1 | 1/2002 | DeSouza |
| 2002/0016540 A1 | 2/2002 | Mikus et al. |
| 2002/0018981 A1 | 2/2002 | Andersson et al. |
| 2002/0029041 A1 | 3/2002 | Hover et al. |
| 2002/0032451 A1 | 3/2002 | Tierney et al. |
| 2002/0038085 A1 | 3/2002 | Immerz |
| 2002/0052606 A1 | 5/2002 | Bonutti |
| 2002/0065461 A1 | 5/2002 | Cosman |
| 2002/0068942 A1 | 6/2002 | Neubauer et al. |
| 2002/0072748 A1 | 6/2002 | Robioneck |
| 2002/0072821 A1 | 6/2002 | Baker |
| 2002/0077533 A1 | 6/2002 | Bieger et al. |
| 2002/0077540 A1 | 6/2002 | Kienzle, III |
| 2002/0085681 A1 | 7/2002 | Jensen |
| 2002/0087101 A1 | 7/2002 | Barrick et al. |
| 2002/0095081 A1 | 7/2002 | Vilsmeier |
| 2002/0102214 A1 | 8/2002 | Briley-Saebo et al. |
| 2002/0107518 A1 | 8/2002 | Neubauer et al. |
| 2002/0115934 A1 | 8/2002 | Tuke |
| 2002/0133161 A1 | 9/2002 | Axelson et al. |
| 2002/0133175 A1 | 9/2002 | Carson |
| 2002/0147455 A1 | 10/2002 | Carson |
| 2002/0151894 A1 | 10/2002 | Melkent et al. |
| 2002/0151898 A1 | 10/2002 | Sohngen et al. |
| 2002/0156371 A1 | 10/2002 | Hedlund et al. |
| 2002/0156479 A1 | 10/2002 | Schulzki et al. |
| 2002/0188194 A1 | 12/2002 | Cosman |
| 2002/0193800 A1 | 12/2002 | Kienzle, III et al. |
| 2002/0198448 A1 | 12/2002 | Zuk et al. |
| 2002/0198451 A1 | 12/2002 | Carson |
| 2002/0198531 A1 | 12/2002 | Millard et al. |
| 2003/0006107 A1 | 1/2003 | Thompson |
| 2003/0018338 A1 | 1/2003 | Axelson, Jr. et al. |
| 2003/0045883 A1 | 3/2003 | Chow et al. |
| 2003/0050643 A1 | 3/2003 | Taft |
| 2003/0055502 A1 | 3/2003 | Lang et al. |
| 2003/0030787 A1 | 4/2003 | Bradbury |
| 2003/0069591 A1 | 4/2003 | Carson et al. |
| 2003/0073901 A1 | 4/2003 | Simon et al. |
| 2003/0153829 A1 | 8/2003 | Sarin et al. |
| 2003/0153859 A1 | 8/2003 | Hinshon |
| 2003/0153978 A1 | 8/2003 | Whiteside |
| 2003/0164172 A1 | 9/2003 | Chumas et al. |
| 2003/0181918 A1 | 9/2003 | Carson |
| 2003/0187351 A1 | 10/2003 | Franck et al. |
| 2003/0187452 A1 | 10/2003 | Smith et al. |
| 2003/0192557 A1 | 10/2003 | Krag et al. |
| 2003/0225329 A1 | 12/2003 | Rossner et al. |
| 2004/0019382 A1 | 1/2004 | Amirouche et al. |
| 2004/0030237 A1 | 2/2004 | Lee et al. |
| 2004/0030245 A1 | 2/2004 | Noble et al. |
| 2004/0039396 A1 | 2/2004 | Couture et al. |
| 2004/0054489 A1 | 3/2004 | Moctezuma De La Barrera |
| 2004/0073279 A1 | 4/2004 | Malackowski et al. |
| 2004/0087852 A1 | 5/2004 | Chen et al. |
| 2004/0097952 A1 | 5/2004 | Sarin et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0152970 A1 | 8/2004 | Hunter et al. |
| 2004/0153079 A1 | 8/2004 | Tsougarakis et al. |
| 2004/0153081 A1 | 8/2004 | Tulkis |
| 2004/0153083 A1 | 8/2004 | Nemec et al. |
| 2004/0167391 A1 | 8/2004 | Solar et al. |
| 2004/0171924 A1 | 9/2004 | Mire et al. |
| 2004/0243481 A1 | 12/2004 | Bradbury et al. |
| 2004/0254586 A1 | 12/2004 | Sarin |
| 2004/0260290 A1 | 12/2004 | Zander et al. |
| 2005/0021037 A1 | 1/2005 | McCombs et al. |
| 2005/0021043 A1 | 1/2005 | Jansen |
| 2005/0075632 A1 | 4/2005 | Russell et al. |
| 2005/0085715 A1 | 4/2005 | Dukesherer et al. |
| 2005/0085822 A1 | 4/2005 | Thornberry et al. |
| 2005/0101966 A1 | 5/2005 | Lavailee |
| 2005/0109855 A1 | 5/2005 | McCombs |
| 2005/0113658 A1 | 5/2005 | Jacobson et al. |
| 2005/0113659 A1 | 5/2005 | Pothier |
| 2005/0113846 A1 | 5/2005 | Carson |
| 2005/0119639 A1 | 6/2005 | McCombs |
| 2005/0119777 A1 | 6/2005 | Arbogast et al. |
| 2005/0124988 A1 | 6/2005 | Terrill-Grisoni et al. |
| 2005/0148843 A1 | 7/2005 | Roose |
| 2005/0149003 A1 | 7/2005 | Tierney et al. |
| 2005/0149041 A1 | 7/2005 | McGinley |
| 2005/0154331 A1 | 7/2005 | Christie et al. |
| 2005/0159759 A1 | 7/2005 | Harbaugh et al. |
| 2005/0177172 A1 | 8/2005 | Acker |
| 2005/0197569 A1 | 9/2005 | McCombs |
| 2005/0197814 A1 | 9/2005 | Aram et al. |
| 2005/0203384 A1 | 9/2005 | Sati et al. |
| 2005/0209726 A1 | 9/2005 | Voit et al. |
| 2005/0216305 A1 | 9/2005 | Funderud |
| 2005/0228266 A1 | 10/2005 | McCombs |
| 2005/0228404 A1 | 10/2005 | Vandevelde |
| 2005/0234332 A1 | 10/2005 | Murphy |
| 2005/0234465 A1 | 10/2005 | McCombs |
| 2005/0234466 A1 | 10/2005 | Stallings |
| 2005/0234468 A1 | 10/2005 | Carson |
| 2005/0245808 A1 | 11/2005 | Carson |
| 2005/0279368 A1 | 12/2005 | McCombs |
| 2005/0288676 A1 | 12/2005 | Schnieders |
| 2006/0015120 A1 | 1/2006 | Richard et al. |
| 2006/0161051 A1 | 7/2006 | Terrill-Grisoni et al. |
| 2006/0190011 A1 | 8/2006 | Landrem |
| 2006/0200025 A1 | 9/2006 | Elliott |
| 2006/0229626 A1 | 10/2006 | McLean |
| 2007/0118055 A1 | 5/2007 | McCombs |
| 2007/0123912 A1 | 5/2007 | Carson |
| 2007/0129629 A1 | 6/2007 | Beauregard et al. |
| 2007/0169782 A1 | 7/2007 | Castleman |
| 2008/0269599 A1 | 10/2008 | Csavoy et al. |

FOREIGN PATENT DOCUMENTS

| | | |
|---|---|---|
| DE | 42 25 112 C1 | 12/1993 |

| | | |
|---|---|---|
| DE | 296 00 990 | 1/1996 |
| DE | 196 29 011 A1 | 1/1998 |
| DE | 197 09 960 A | 9/1998 |
| DE | 197 09 960 A1 | 9/1998 |
| DE | 299 06 438 U1 | 9/1999 |
| DE | 296 23 941 U1 | 11/2000 |
| DE | 200 21 494 | 3/2001 |
| DE | 201 03 416 U1 | 7/2001 |
| DE | 100 12 042 | 8/2001 |
| DE | 100 31 887 A1 | 1/2002 |
| DE | 102 07 035 | 2/2002 |
| DE | 100 45 381 A1 | 4/2002 |
| DE | 202 13 243 | 10/2002 |
| DE | 203 09 399 | 8/2003 |
| EP | 0 327 509 A1 | 8/1989 |
| EP | 0 327 509 B1 | 8/1989 |
| EP | 0 337 901 A1 | 10/1989 |
| EP | 0 340 176 A2 | 11/1989 |
| EP | 0 216 794 B1 | 12/1989 |
| EP | 0 366 488 B1 | 5/1990 |
| EP | 0 376 657 B1 | 7/1990 |
| EP | 0 380 451 A2 | 8/1990 |
| EP | 0 415 837 A2 | 3/1991 |
| EP | 0 466 659 A2 | 1/1992 |
| EP | 0 359 097 | 8/1992 |
| EP | 0 538 152 A1 | 4/1993 |
| EP | 0 538 153 B1 | 4/1993 |
| EP | 0 555 003 B1 | 8/1993 |
| EP | 0 428 303 | 7/1995 |
| EP | 0 676 178 A | 10/1995 |
| EP | 0 720 834 A2 | 7/1996 |
| EP | 0 619 097 | 6/1999 |
| EP | 1 149 562 A2 | 10/2001 |
| EP | 1 033 108 | 2/2002 |
| EP | 1 190 676 B1 | 3/2002 |
| EP | 1 226 788 | 7/2002 |
| EP | 1 226 788 A1 | 7/2002 |
| EP | 0 782 842 | 9/2002 |
| EP | 1 236 450 A1 | 9/2002 |
| EP | 1 249 207 | 10/2002 |
| EP | 1 348 384 | 10/2003 |
| EP | 1 384 456 A2 | 1/2004 |
| EP | 1 405 603 A2 | 4/2004 |
| EP | 1 406 203 | 4/2004 |
| EP | 1 435 223 A1 | 7/2004 |
| EP | 1 442 715 | 8/2004 |
| EP | 1 459 686 A2 | 9/2004 |
| EP | 1 532 946 A2 | 5/2005 |
| EP | 1 563 795 | 8/2005 |
| FR | 742618 | 3/1933 |
| FR | 2 828 397 | 2/2003 |
| GB | 2 224 937 | 5/1990 |
| GB | 2 397 769 A | 8/2004 |
| JP | 2002-304439 | 10/2002 |
| WO | WO 86/05384 | 9/1986 |
| WO | WO 89/09570 | 10/1989 |
| WO | WO 9325157 | 12/1993 |
| WO | WO 94/17733 | 8/1994 |
| WO | WO 95/15714 | 6/1995 |
| WO | WO 96/35387 | 11/1996 |
| WO | WO 97/16129 | 5/1997 |
| WO | WO 97/23172 | 7/1997 |
| WO | WO 97/29683 | 8/1997 |
| WO | WO 98/29032 | 7/1998 |
| WO | WO 98/46169 | 10/1998 |
| WO | WO 99/15097 | 4/1999 |
| WO | WO 99/27860 | 6/1999 |
| WO | WO 99/60939 | 12/1999 |
| WO | WO 99/65380 | 12/1999 |
| WO | WO 00/00093 | 1/2000 |
| WO | WO 00/21442 | 4/2000 |
| WO | WO 00/47103 | 8/2000 |
| WO | WO 00/64367 | 11/2000 |
| WO | WO 01/01845 A2 | 1/2001 |
| WO | WO 01/19271 A2 | 3/2001 |
| WO | WO 01/34050 A2 | 5/2001 |
| WO | WO 01/34050 A3 | 5/2001 |
| WO | WO 01/64124 A1 | 9/2001 |
| WO | WO 01/67979 A1 | 9/2001 |
| WO | WO 01/91647 A1 | 12/2001 |
| WO | WO 01/93770 A1 | 12/2001 |
| WO | WO 02/24096 A1 | 3/2002 |
| WO | WO 02/41794 A1 | 5/2002 |
| WO | WO 02/063236 A1 | 8/2002 |
| WO | WO 02/063236 A3 | 8/2002 |
| WO | WO 02/064042 | 8/2002 |
| WO | WO 02/067783 | 9/2002 |
| WO | WO 02/067784 | 9/2002 |
| WO | WO 02/067800 | 9/2002 |
| WO | WO 02/067880 | 9/2002 |
| WO | WO 02/080824 A1 | 10/2002 |
| WO | WO 03/006107 | 1/2003 |
| WO | WO 03/015642 | 2/2003 |
| WO | WO 03/030787 | 4/2003 |
| WO | WO 03/034213 A2 | 4/2003 |
| WO | WO 03/034933 A1 | 5/2003 |
| WO | WO 03/037192 A1 | 5/2003 |
| WO | WO 03/039377 | 5/2003 |
| WO | WO 03/041566 A2 | 5/2003 |
| WO | WO 03/065931 | 8/2003 |
| WO | WO 03/065949 A2 | 8/2003 |
| WO | WO 03/068090 A1 | 8/2003 |
| WO | WO 03/071969 A1 | 9/2003 |
| WO | WO 03/075740 A2 | 9/2003 |
| WO | WO 03/079940 | 10/2003 |
| WO | WO 03/096870 A2 | 11/2003 |
| WO | WO 2004/001569 A2 | 12/2003 |
| WO | WO 2004/017842 A2 | 3/2004 |
| WO | WO 2004/019792 | 3/2004 |
| WO | WO 2004/029908 A1 | 4/2004 |
| WO | WO 2004/030556 A2 | 4/2004 |
| WO | WO 2004/030559 A1 | 4/2004 |
| WO | WO 2004/046754 A2 | 6/2004 |
| WO | WO 2004/069036 | 8/2004 |
| WO | WO 2004/070580 | 8/2004 |
| WO | WO 2004/008740 A1 | 10/2004 |
| WO | WO 2004/084740 | 10/2004 |
| WO | WO 2005/009303 A1 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO2005/048851 A1 | 6/2005 |
| WO | WO2005/053559 A1 | 6/2005 |
| WO | WO 2005/057439 | 6/2005 |
| WO | WO2005/070312 A1 | 8/2005 |
| WO | WO 2005/070319 A1 | 8/2005 |
| WO | WO 2005/072629 A1 | 8/2005 |
| WO | WO 2005/096982 | 10/2005 |
| WO | WO 2005/0104977 | 11/2005 |
| WO | WO 2005/0104978 | 11/2005 |
| WO | WO 2006/044367 A1 | 4/2006 |
| WO | WO 2006/060631 A1 | 6/2006 |
| WO | WO 2006/078236 A1 | 7/2006 |
| WO | WO 2008/021494 | 2/2008 |
| WO | WO 2008/064126 A2 | 5/2008 |

OTHER PUBLICATIONS

Hafez, et al., 'Computer-assisted Total Knee Arthroplasty Using Patient-specific Templating,' *Clinical Orthopaedics and Related Research*, No. 444, pp. 184-192 (2006).

English-language abstract of CN 101224104 published on Jul. 23, 2008, Quan, Renfu, et al., Inventors.

National Institute of Arthritis and Musculoskeletal and Skin Diseases (NIAMS), "Questions & Answers about . . . Knee Problems", 36 pp. (May 2001).

"Implant" Merriam-Webster Online Dictionary [online], Retrieved from the Internet <URL: www.m-w.com.

Delp, et al., "Computer Assisted Knee Replacement," *Clinical Orthopaedics and Related Research*, 354:49-56 (1998).

DiGiola, et al., Computer Assisted Orthopaedic Surgery, *Clinical Orthopaedics and Related Research*, 354:8-16 (1998).

Simon, et al., "The Fundamentals of Virtual Fluoroscopy," *The Fundamentals of Virtual Fluoroscopy*, pp. 57-61 (undated).

Stryker Navigation System Brochure entitled ". . . best alignment for gap kinematics," 2 pages (undated).

BrainLab Brochure, pp. 1-28 (undated).

Barnes, et al., "Unicompartmental Knee Arthroplasty," *Bombay Hospital Journal*, Issue Special, pp. 1-5, www.bhj.org/journal/1996/3803_july/special_486.htm.

Bonutti, et al., "Minimal Incision Total Knee Arthroplasty Using the Suspended Leg Technique," *Orthopedics*, (published Sep. 2003), 6 pages http://www.orthobluejournal.com/0903/9tips.asp.

Bonutti, "Total Joint Replacement Surgery in the $21^{st}$ Century—New 'Limited-Incision' Total Knee Replacement Offers Important Advantages," 01 page (undated).

Croitoru, et al., "Fixation-Based Surgery: A New Technique for Distal Radius Osteotomy," *Clinical Paper, Computer Aided Surgery* 2001, 160-169, vol. 6 (2001).

Delp, et al., "Computer-Assisted Knee Replacement," *Clinical Orthopaedics and Related Research*, 354:49-56 (1998).

Deluzio, et al., "Static alignment and the adduction moment in unicompartmental arthroplasty patients," Presented at NACOB 98: North American Congress on Biomechanics, University of Waterloo, Ontario, Canada, Aug. 14-18, 1998.

DiGioia, et al., "Computer Assisted Orthopedic Surgery," *Clinical Orthopaedics and Related Research*, Sep. 1998, vol. 354, pp. 8-16.

Ellis, et al., "A Surgical Planning and Guidance System for High Tibial Osteotomy," *Journal of Computer-Assisted Surgery*, 4(5):264-274 (1999).

Foley, et al., "Percutaneous pedicle screw fixation of the lumbar spine," *Neurosurg. Focus*, vol. 10(4), pp. 1-8 (2001).

Glossop, http:/www/traxta.com/papers/cua/mode1.html, 8 pages (Feb. 6, 2002).

Iyun, et al., "Planning and Performing the Ilizarov Method with the Taylor Spatial Frame," Abstract, at $2^{nd}$ Annual Meeting of International Society for Computer Assisted Orthopaedic Surgery, Jun. 21, 2002, pp. 145-147.

Kanade, et al., "Image-Based Computer Assisted Orthopedic Surgery System," Bonecraft, Inc., 12 pages, Apr. 30, 2001.

Kiefer, et al., "Computer Aided Knee Arthroplasty Versus Conventional Technique—First Results," First Annual Meeting of the International Society for Computer Assisted Orthopedic Surgery, Davos, Switzerland, Feb. 8-10, 2001.

Kunz, et al., "Development and Verification of a Non-CT Based Total Knee Arthroplasty System for the LCS Prosthesis," First Annual Meeting of the International Society for Computer Assisted Orthopedic Surgery, Davos, Switzerland, Feb. 8-10, 2001.

Munoz, et al., "Computer Assisted Planning of Hig Tibial Osteotomy for the Treatment of Knee Osteoarthritis," http://www.utc.fr/esb/esb09/abs_htm/570.html (Feb. 21, 2002) (three pages).

Picard, et al., "Kneenav.TKR: Concept and Clinical Application," Computer Assisted Orthopedic Surgery USA 2000 Meeting, Pittsburgh, PA., Jun. 15-17, 2000.

Saragaglia, et al., "Computer Assisted Total Knee Arthroplasty: Comparison with a Conventional Procedure. Results of a 50 Cases Prospective Randomized Study," First Annual Meeting of the International Society for Computer Assisted Orthopedic Surgery, Davos, Switzlerland, Feb. 8-10, 2001.

Simon, et al., "The Fundamentals of Virtual Fluoroscopy," Medtronic Surgical Navigation Technologies, Medtronic, pp. 57-66, Computer Assisted Orthopedic Surgery USA 2000 Meeting, Pittsburgh, PA, Jun. 15-17, 2000.

Sugano, et al., "Medical Robotics and Computer-Assisted Surgery in the Surgical Treatment of Patients and Rheumatic Diseases," *Cutting Edge Reports*, http://www/rheuma2lst.com/archives/cutting_edge_Robotics_Japan.html (Apr. 27, 2000).

Suhm, et al., "Adapting the C-Arm Fluoroscope for Image Guided Orthopaedic Surgery," *CAOS*, pp. 212-214 (2002).

Tenbusch, et al., "First Results Using the Robodoc® System for Total Knee Replacement," First Annual Meeting of the International Society for Computer Assisted Orthopedic Surgrey, Davos, Switzerland, Feb. 8-10, 2001.

Valstar, et al., "Towards computer-assisted surgery in should joint replacement," *ISPRS Journal of Photogrammetry & Remote Sensing*, 56:326-337 (2002).

Stryker Navigation System brochure entitled ". . . best alignment for gap kinematics," 6 pages (2001).

BrainLAB Brochure entitled "Ortho . . . Your Partner for the Future" pp. 1-28 (2002).

Search Evolution Total Knee System—Relax—B. Braun Melsungen AG website http://www.orthopilot.com/index.cfm?uuid=26EA6AA4838D495B8A895420A83BD099&obj (3 pages, Sep. 2, 2003).

Patent Abstracts of Japan, vol. 2002, No. 5, May 3, 2002 & JP 2002 017740A (Ochi Takahiro; Yonenobu Sakuo: MMT:KK) Jan. 22, 2002 Abstract.

iON™ Smith & Nephew Orthopaedics Brochure entitled "You'll Never Look At Your Patients the Same Way Again." 10 pages (Jan. 2001).

Smith & Nephew—Orthopaedics—TriGen Reducer http://www.smithnephew.com/US/Standard.asp?NodeID=2996, one page (Jan. 21, 2003).

Smith & Nephew—Orthopaedics—TriGen Flexible Reamer System http://www.smithnephew.com/US/Standard.asp?NodeID=2998, 2 pages (Jan. 21, 2003).

AO Development Institute "MEPUC Motorized Exact Positioning Unit . . . " one page (Mar. 26, 2003) http://www/ao-asif.ch/development/adi/examples/mepuc.shtml.

AO Development Institute "MEPUC Motorized Exact Positioning Unit for C-arm," one page (Jul. 7, 2003) http://www.ao-asif.ch/development/adi/examples/mepuc.shtml.

Smith & Nephew—Orthopaedics—CAS—Knees Computer Assisted Total Knee Replacement Surgery, 2 pages (Oct. 13, 2004) http:ortho.smith-nephew.com/us/Standard.asp?NodeId=3396.

Smith & Nephew Orthopaedic product bulletin , 1 page.

Smith & Nephew Brochure entitled "Surgical Technique Mini Incision Hip Posterior Approach," 20 pages (Mar. 2003).

Tricon Total Knee System, "Tricon-M® with PRO-FIT™ Surgical Procedures," Richards Brochure, pp. 1-29 (undated).

Smith & Nephew Richards Genesis® Total Knee System, "Revision Posterior Referencing Instrumentaion Surgical Technique," Brochure, pp. 1-51 (Dec. 1993).

Smith & Nephew Richards Genesis® "Total Knee System Primary Surgical Technique Anterior Referencing Instrumentation," pp. 59 (Dec. 1993).

Smith & Nephew Genesis II "Total Knee System Primary Surgical Technique," Brochure, pp. 1-36 (Mar. 2001).

Smith & Nephew First Choice in Orthopaedics Brochure Entitled "Achieve Computer Assisted Surgery Trauma Applications The Orbiter Base Station & Satellite Surgical Platform," 18 pages (undated).

Medtronic Surgical Navigation Technologies SNT Vertek photograph, one page (undated).

Medtronic Surgical Navigation Technologies System Components photograph Vertek Platform, one page (undated).

Medtronic Surgical Navigation Technologies "Overview Image-Guided Surgery An Advanced Solution to Traditional Surgery," two pages (undated).

Bonecraft Carnegie Mellon Computer-Aided Bone Deformity Correction Brochure, pp. 1-5 (undated).

Smith & Nephew Total Hip Replacement Surgery, HipReplacementInfo.com. 3 pages, Nov. 8, 2005 http://www/hipreplacementinfo.com/hip-total-replacement.htm.

Smith & Nephew Brochure, Design Features, "Opera" pp. 4-15 (1999).

Corinth Surgeon Performs Revolutionary Hip Replacement , Mississippi Medical News, pp. 1-2 (Nov. 17, 2005) http://host1.bondware.com/~mississippi/news.php?viewStory=347.

Dario, et al., 'Smart Surgical Tools and Augmenting Devices,' IEEE Trans. Rob. Autom., 19(5):782-792 (2003).

Fernandez-Lozano, et al., 'Human-machine interface evaluation in a computer assisted surgical system,' Proc. IEEE Int. Conf. Rob. Autom., 2004:231-236 (2004).

Martelli, et al., 'Criteria of interface evaluation for computer assisted surgery systems,' Int. J. Med. Informatics, 72:35-45 (2003).

Visarius, et al., 'Man-machine interfaces in computer assisted surgery,' Computer Aided Surgery, pp. 102-107 (2004).

Radermacher, et al., "Computer Assisted Orthopaedic Surgery with Image Based Individual Templates," Clinical Orthopaedics and Related Research, 354:28-38 (1998).

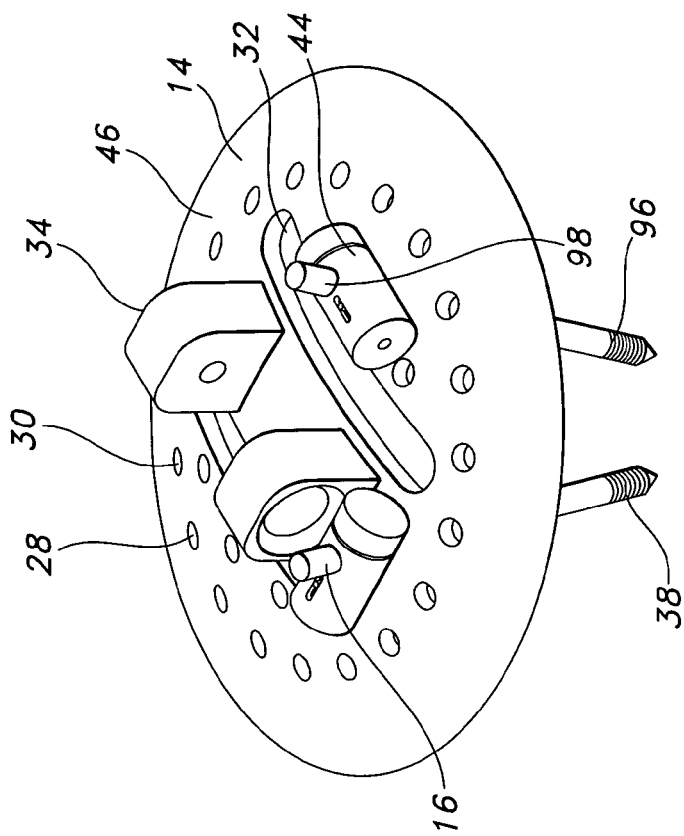
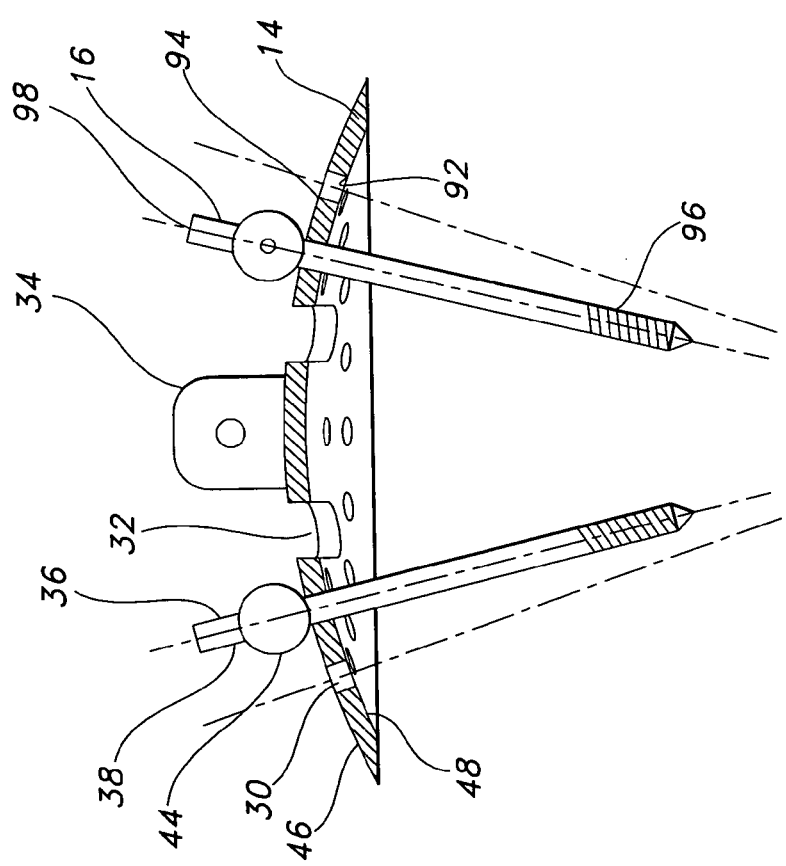
FIG. 8
FIG. 7

SURGICAL POSITIONERS

BACKGROUND

A major concern during surgical procedures as well as other medical operations is carrying out the procedures with as much precision as is possible. For example, in orthopedic procedures, less than optimum alignment of implanted prosthetic components may cause undesired wear, which may eventually lead to the failure of the implanted prosthesis and necessitate revision. Other general surgical procedures, such as body exploration from penetrating trauma, implant placement and neoplasm surgery, also require precision in their execution.

With orthopedic procedures, previous practices have made precise alignment of prosthetic components challenging. For example, in a total knee arthroplasty, previous instrument design for resection of bone limited the alignment of the femoral and tibial resections to average values for varus/valgus, flexion/extension and external/internal rotation. Additionally, surgeons often use visual landmarks or "rules of thumb" for alignment, which can be misleading due to anatomical variability. Intramedullary referencing instruments are also undesirable because they violate the femoral and tibial canals, increasing the risk of fat embolism and unnecessary blood loss in the patient. Similar problems may also be encountered in other procedures, such as the replacement of hip and shoulder joints as well as the insertion of an intramedullary canal nail into a weakened or broken bone.

Several manufacturers currently produce image-guided surgical navigation systems that are used to assist in performing surgical procedures with greater precision. The TREON™ and iON™ systems with FLUORONAV™ software manufactured by Medtronic Surgical Navigation Technologies, Inc. are examples of such systems. The BrainLAB VECTORVISION™ system is another example of such a surgical navigation system. Systems and processes for accomplishing image-guided surgery are also disclosed in U.S. Ser. No. 10/084,012, filed Feb. 27, 2002 and entitled "Total Knee Arthroplasty Systems and Processes"; U.S. Ser. No. 10/084,278, filed Feb. 27, 2002 and entitled "Surgical Navigation Systems and Processes for Unicompartmental Knee Arthroplasty"; U.S. Ser. No. 10/084,291, filed Feb. 27, 2002 and entitled "Surgical Navigation Systems and Processes for High Tibial Osteotomy"; International Application No. US02/05955, filed Feb. 27, 2002 and entitled "Total Knee Arthroplasty Systems and Processes"; International Application No. US02/05956, filed Feb. 27, 2002 and entitled "Surgical Navigation Systems and Processes for Unicompartmental Knee Arthroplasty"; International Application No. US02/05783 entitled "Surgical Navigation Systems and Processes for High Tibial Osteotomy"; U.S. Ser. No. 10/364,859, filed Feb. 11, 2003 and entitled "Image Guided Fracture Reduction," which claims priority to U.S. Ser. No. 60/355,886, filed Feb. 11, 2002 and entitled "Image Guided Fracture Reduction"; and U.S. Ser. No. 60/271,818, filed Feb. 27, 2001 and entitled "Image Guided System for Arthroplasty"; U.S. Ser. No. 10/229,372, filed Aug. 27, 2002 and entitled "Image Computer Assisted Knee Arthroplasty", the entire contents of each of which are incorporated herein by reference as are all documents incorporated by reference therein.

These systems and processes use position and/or orientation tracking sensors such as infrared sensors acting in a stereoscopic manner or other sensors acting in conjunction with reference structures or reference transmitters to track positions of body parts, surgery-related items such as implements, instruments, trial prosthetics, prosthetic components, and virtual constructs or references such as rotational axes which have been calculated and stored based on designation of bone landmarks. Processing capability such as any desired form of computer functionality, whether standalone, networked, or otherwise, takes into account the position and orientation information as to various items in the position sensing field (which may correspond generally or specifically to all or portions or more than all of the surgical field) based on sensed position and orientation of their associated reference structures such as fiducials, reference transmitters, or based on stored position and/or orientation information. The processing functionality correlates this position and orientation information for each object with stored information, such as a computerized fluoroscopic imaged file, a wire frame data file for rendering a representation of an instrument component, trial prosthesis or actual prosthesis, or a computer generated file relating to a rotational axis or other virtual construct or reference. The processing functionality then displays position and orientation of these objects on a screen or monitor. Thus, these systems and processes, by sensing the position of reference structures or transmitters, can display or otherwise output useful data relating to predicted or actual position and orientation of body parts, surgically related items, implants, and virtual constructs for use in navigation, assessment, and otherwise performing surgery or other operations.

Some of these reference structures or reference transmitters may emit or reflect infrared light that is then detected by an infrared camera. The references may be sensed actively or passively by infrared, visual, sound, magnetic, electromagnetic, x-ray, or any other desired technique. An active reference emits energy, and a passive reference merely reflects energy. In some embodiments, the reference structures have at least three, but usually four, markers or fiducials that are tracked by an infrared sensor to determine the position and orientation of the reference and thus the position and orientation of the associated instrument, implant component or other object to which the reference is attached.

The Medtronic imaging systems allow reference structures to be detected at the same time the fluoroscopy imaging is occurring. This allows the position and orientation of the reference structures to be coordinated with the fluoroscope imaging. Then, after processing position and orientation data, the reference structures may be used to track the position and orientation of anatomical features that were recorded with a fluoroscope. Computer-generated images of instruments, components, or other structures that are fitted with reference structures may be superimposed on the fluoroscopic images. The instruments, trial, implant or other structure or geometry can be displayed as 3-D models, outline models, or bone-implant interface surfaces.

The reference structures described above are an important component of these systems and processes. FIG. 1 shows a reference structure 8 secured to a bone. FIG. 2 shows reference structures 8 as used in a surgical setting. In some systems, a reference transmitter, as opposed to a passive reference structure, actively transmits position and orientation data to the tracking system. FIG. 3 shows a reference transmitter or receiver 10 secured to a bone that is useable with such systems.

Systems such as the Medtronic system may monitor the location and orientation of the reference structures 8, and consequently the portion of the anatomy or instruments secured to the reference structure 8, by either actively or passively detecting the position of fiducials 12 shown in FIGS. 1 and 2 associated with the reference structure 8. Because the fiducials 12 can be arranged in particular patterns, the system can determine the exact orientation and location of the reference structure 8 associated with the fiducials 12. In other words, depending upon the particular location of the individual fiducials 12, the system will "see" the reference structure 8 in a particular way and will be able to calculate the location and orientation of the reference structure based upon that data. Consequently, the system can determine the exact orientation and location of the portion of the anatomy or instrument associated with and connected to the reference structure 8.

As discussed above, the exact spatial relationship of the individual fiducials 12 with respect to each other and the associated anatomy or instrument forms the basis of how a fiducial-based system calculates the position and orientation of the associated items. Similarly, the exact spatial relationship of a reference transmitter or receiver 10 with respect to its associated anatomy or instrument forms the basis of how a transmitter-based system calculates the position and orientation of the associated anatomy or instruments. Consequently, once the spatial relationship of the fiducials 12 or reference transmitter or receiver 10 with respect to the associated item to be tracked has been registered in the system, subsequent changes in the position and/or orientation of the fiducials 12 or reference transmitter 10 may cause the system to erroneously calculate the position and orientation of the anatomy or instruments associated with the fiducials 12 or reference transmitter 10. Even minor changes in orientation and/or position of the references may lead to dramatic differences in how the system detects the orientation and/or location of the associated anatomy or instruments. Such changes may require the system to be recalibrated, requiring additional fluoroscopy or other imaging to be obtained, increasing the time and the expense of the procedure. Failure to recalibrate the system may lead to imprecision in the execution of the desired surgical procedure.

The references 8 and 10 shown in FIGS. 1-3 may be undesirable because they may be particularly vulnerable to change of location and/or orientation with respect to their associated instrument or anatomy. This may be especially problematic in busy operating rooms, where several people are working at once. References 8 and 10 may be particularly susceptible to being bumped, dislodged, or otherwise misplaced because they are cumbersome and prone to interfering with the surgical procedure because of their size. The references may also be susceptible to change in location and/or orientation because they are secured at a single location by a column or other structure to the bony anatomy, instruments, or other structure and are distanced from the anatomy to which they are attached.

Some reference structures do not allow the repositioning or removal of individual fiducials with respect to the reference structure. This may be problematic because there may be times when it is desirable to place the reference structure in a location and orientation that can be effectively visualized and tracked by the system, yet remain out of the way of the surgeon. Moreover, reference structures that do not allow removal of the fiducials from the remainder of the reference structure prevent defective or inoperative fiducials from being replaced without replacing the entire reference structure.

Another major concern with carrying out surgeries and other medical operations with absolute precision is precisely targeting, aligning and/or navigating instruments with or without the assistance of image-guided surgical navigation systems. Problematically, during surgery a surgeon may need to use one hand to stabilize an instrument while using the other hand to target, align and/or navigate the instrument. If the surgeon is the sole means for stabilizing as well as aligning/navigating/targeting the instrument, distractions to the surgeon may result in the instrument becoming misaligned, increasing the chances for surgical error and/or increasing procedural tedium. For instance, if the surgeon looks away from the instrument to view a monitor, the surgeon may inadvertently move his or her hands, causing the instrument to move relative to the anatomy.

Some efforts to alleviate the above difficulties include the use of robotic arms. However, robotic arms may require the navigation of the instrument to be programmed and consequently executed without surgeon input during the robotic portion of the procedure. These robotic arms may be undesirable because they prevent the surgeon from using his or her intuition and experience to target, align and/or navigate the instrument. Additionally, these robotic arms prevent the surgeon from receiving tactile feedback, an important part of some surgical procedures. In addition, robots generally operate much more slowly than a skilled surgeon.

Other, non-robotic, instrument mounting arms have also been used to lock a navigated instrument into position. In addition to the other problems mentioned above, some previous instrument mounting arms may be undesirable because readjustment of the instrument, once locked into place, requires unlocking the arm. Unlocking the arm may increase the tedium of the procedure.

SUMMARY

Various aspects and embodiments of the present invention include surgical positioners capable of increasing surgical precision, as well as methods and procedures for utilizing the surgical positioners. These surgical positioners include certain platforms, which are securable to an individual's anatomy, each other, and/or any other desired structure. These platforms may be modular in nature, allowing various surgical items to be secured and/or stabilized in various orientations and locations. They provide stable bases for locating surgical items, including surgical references useful in conjunction with image-guided surgical navigation systems ("tracking systems"), such as the systems discussed above. These platforms may also be used as stable bases for other surgical instruments, used with or without tracking systems, including drills, reamers, surgical guides or any other desired instrumentation. These platforms may also be used to guide the installation of surgical implants, such as intramedullary nails. Consequently, various embodiments of the present invention allow ease of securing, locating, mounting, stabilizing, navigating, targeting, positioning and/or aligning surgical items relative to an individual's anatomy, thereby improving the precision with which surgical procedures may be performed.

In some embodiments, the stabilizer platform is adapted to contact an individual' In certain embodiments, a stabilizer platform is adapted to contact an individual's skin at least at three points on a surface of the platform; adapted to be biased against the individual's skin by at least two fasteners, each of the fasteners connected to bone of the individual such that at least one of the fasteners is not parallel to at least one other of the fasteners; and adapted to support at least one item.

In some embodiments, the stabilizer platform is adapted to contact an individual's skin at at least three points. The stabilizer platform may be biased against the individual by a number of fasteners such that at least two of the fasteners are not parallel with respect to one another. Biasing the platform against the individual's skin in this manner may secure the platform to the individual's anatomy in a stable manner. The non-parallel orientation of the fasteners may resist various pushing, pulling, twisting and/or other forces applied intentionally or accidentally to the fasteners, the stabilizer platform or other items secured to the stabilizer platform. In some embodiments, the stabilizer platform can be adapted such that at least some of the fasteners converge towards one another, creating an especially stable relationship between the stabilizer platform and the individual's anatomy.

Other embodiments according to certain aspects of this invention provide methods and procedures for utilizing, securing, stabilizing and aligning various surgical referencing positioners, navigating positioners, and other items with respect to a portion of an individual's anatomy. These methods secure the stabilizer platform to the individual's anatomy such that it is less likely to be dislodged or repositioned due to inadvertent contact.

In some embodiments, the surgical positioners may include a surgical item positioner. The surgical item positioner, which may include a stabilizing system (such as, but not limited to stabilizer platforms coupled with arms) and an support platform adapted to connect to the stabilizing system, may assist a surgeon to precisely navigate, align, position, secure and/or balance a surgical item during surgical procedures. The surgical instrument positioner may include a support platform. The support platform may be similar to or different from the stabilizer platform.

In some embodiments, the surgical item positioner may include a support platform and a stabilizing system. The support platform may be adapted to contact an individual's skin at least at three points on a surface of the platform and support at least one item; and may be adapted to connect to a stabilizing system. The stabilizing system may be adapted to connect to the support platform, stabilize the support platform, and be biased against the individual by at least one fastener. The stabilizing system, biased against a portion of an individual's anatomy, may stabilize the support platform.

Some embodiments of the present invention include a method of establishing a reference for use as a navigational aid in surgery, the reference being less likely to be accidentally repositioned during surgical procedures. The method may include: positioning and securing a first modular fiducial to a structure; positioning and securing a second modular fiducial to the structure, the second modular fiducial able to be positioned at least somewhat independently of the first modular fiducial; and positioning and securing at least one additional modular fiducial to the structure, the at least one additional modular fiducial able to be positioned at least somewhat independently of the first modular fiducial and the second modular fiducial. The first, second and at least one additional modular fiducials may be positioned in one of a plurality of patterns, some of the patterns recognizable by a tracking system such that the tracking system can track the position and orientation of the pattern.

Establishing a reference using modular fiducials may provide a surgical reference that is less likely to be repositioned due to undesired or unintended contact. References formed from modular fiducials may also allow placing the fiducials in locations that maximize visibility to the tracking system while remaining out of the surgeon's way.

In some embodiments, the referenced item may be a surgical item, such as a platform, drill, drill-guide, working channel, trial implant or any other desired item. In embodiments where a platform is the referenced item, tracking the platform may also allow tracking of the anatomical structure to which the platform is secured. In other embodiments, the modular fiducials may be individually and directly attached to the anatomical structure.

Other aspects and embodiments of the present invention will become apparent by reference to the remainder of this document.

STATEMENT OF INVENTION

In accordance with aspects of the present invention, there is provided:

A surgical positioner for supporting items used in surgery, the surgical positioner comprising a platform characterized in that the platform includes structure which is adapted to: (i) contact an individual's skin at least at three points on a surface of the platform; (ii) be biased against the individual's skin by at least two fasteners, each of the fasteners connected to bone of the individual such that at least one of the fasteners is not parallel to at least one other of the fasteners; and (iii) support at least one item by capturing a portion of the item.

A surgical positioner further characterized in that the platform includes a plurality of apertures defined by portions of the platform, at least one of the apertures adapted to receive one of the fasteners.

A surgical positioner further characterized in that the platform includes a first platform surface and a second platform surface, at least some of the plurality of apertures extending from the first platform surface to the second platform surface, the first platform surface defining a convex surface and the second platform surface defining a concave surface.

A surgical positioner further characterized in that at least two of the apertures are each adapted to receive one of the fasteners such that the at least two fasteners received by the apertures converge towards each other.

A surgical item positioner for supporting an item used in surgery characterized in that the surgical positioner includes:
  (a) a support platform adapted to: (i) contact an individual's skin at least at three points on a surface of the platform; (ii) support at least one item; and (iii) be connected to a stabilizing system; and
  (b) the stabilizing system, the stabilizing system adapted to: (i) connect to the support platform; (ii) stabilize the support platform; and (iii) be biased against the individual by at least one fastener.

A surgical item positioner further characterized in that the stabilizing system comprises:
  (a) a stabilizer platform, the stabilizer platform adapted to: (i) contact an individual's skin at least at three points on a surface of the stabilizer platform; (ii) be biased against the individual's skin by at least two fasteners such that at least one of the fasteners is not parallel to at least one other of the fasteners; and (iii) be connected to the support platform by an arm; and
  (b) the arm, the arm adapted to connect the support platform to the stabilizer platform.

A surgical item positioner further characterized in that the stabilizer platform is adapted to receive the at least two fasteners such that the at least two fasteners converge towards each other, the at least two fasteners adapted to be secured to the bony anatomy of the individual.

A surgical item positioner further characterized in that the arm comprises a flexible arm.

A surgical item positioner further characterized in that portions of the support platform define a portal, the portal adapted to receive the at least one item.

A surgical item positioner further characterized in that the portal is adapted to interact with a bearing in a rotating fashion, the bearing adapted to interact with portions of the item in a rotating and sliding fashion.

A surgical item positioner further characterized in that the bearing further comprises a plurality of protrusions extending from an outer surface of the bearing, at least some of the protrusions adapted to interact with a channel at least partially extending around an interior circumference of the portal.

A reference for use as a navigational positioner in surgery characterized in that the reference includes:

(a) a first modular fiducial secured to a structure;

(b) a second modular fiducial secured to the structure, the second modular fiducial positioned at least somewhat independently of the first modular fiducial; and (c) at least one additional modular fiducial secured to the structure, the at least one additional modular fiducial positioned at least somewhat independently of the first modular fiducial and the second modular fiducial, wherein the first, second and at least one additional modular fiducials are positioned in one of a plurality of patterns, some of the patterns recognizable by a tracking system such that the tracking system can track the position and orientation of the pattern.

A reference further characterized in that portions of the first, second and at least one additional modular fiducials are captured and supported by a platform adapted to: (i) contact an individual's skin at least at three points on a surface of the platform; and (ii) be biased against the individual's skin by at least two fasteners, each of the fasteners connected to bone of the individual such that at least one of the fasteners is not parallel to at least one other of the fasteners.

A reference further characterized in that the first, second and at least one additional modular fiducials are captured and supported by a plurality of apertures defined by the platform.

A reference further characterized in that the first, second and at least one additional modular fiducials are secured to a portion of an individual's bony anatomy.

BRIEF DESCRIPTION OF THE DRAWINGS

FIG. 7 shows a side sectional schematic view of a stabilizer platform according to another embodiment of the present invention.

FIG. 8 shows a perspective view of a stabilizer platform according to another embodiment of the present invention.

DETAILED DESCRIPTION

Figure 4:
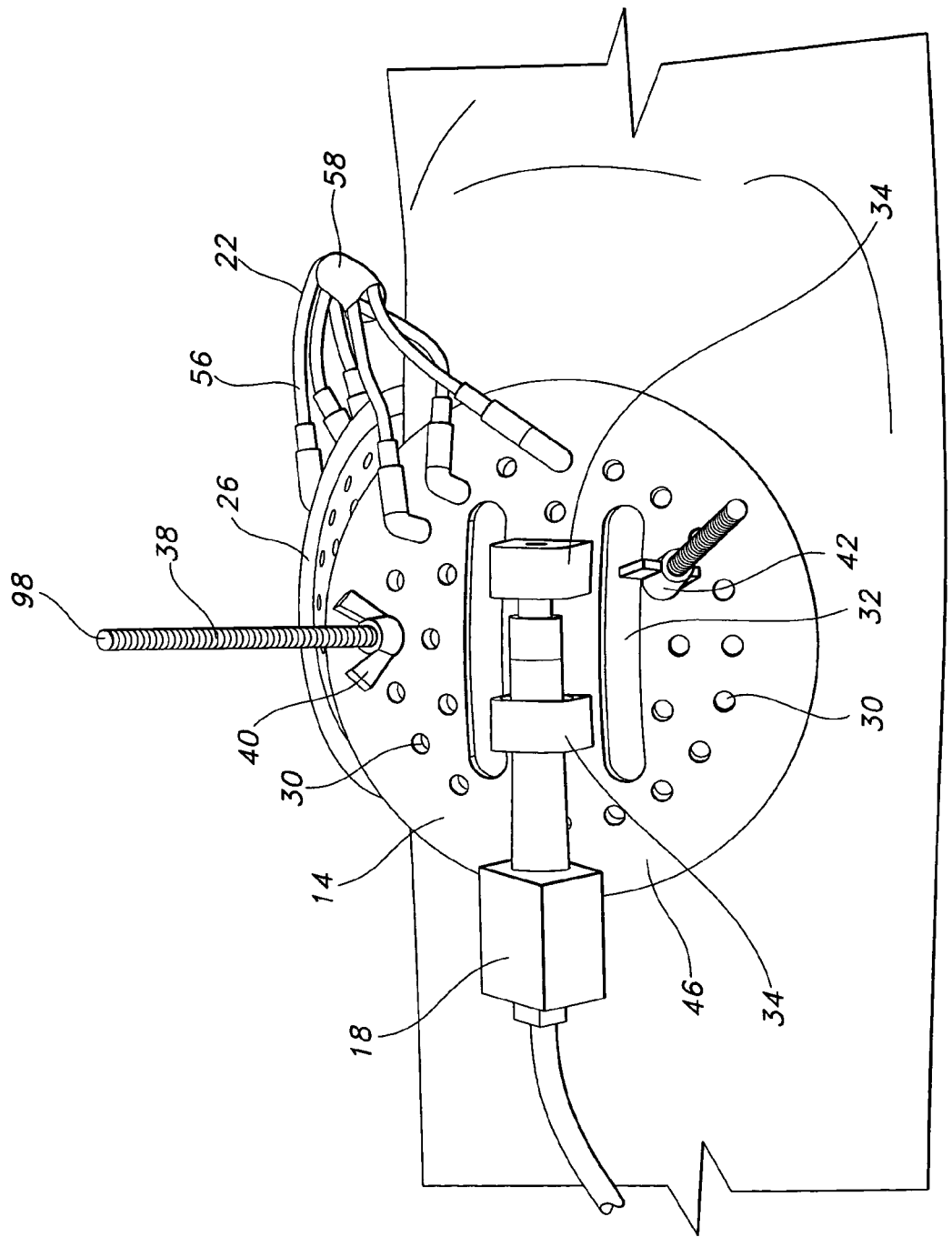
FIG. 4 shows a perspective view of a stabilizer platform according to a first embodiment of the present invention biased against an individual's skin.

FIG. 4 shows a platform 14 according to various aspects and embodiments of the present invention. The platform 14 may be used as a stabilizer platform by being biased against portions of an individual's anatomy to provide a stable and low profile platform for securing other items that may be useful in various surgical procedures. Items may be secured to or stabilized by stabilizer platform 14 in a releasable, rigid and/or movable manner.

Stabilizer platform 14 may be formed from any desired and suitable material and in any desired and suitable method. For instance, in some embodiments, stabilizer platform 14 may be formed from high impact, vacuum molded plastic. In other embodiments, stabilizer platform 14 may be machined from stainless steel or aluminum.

Any desired item may be supported by stabilizer platform 14. Various items that may be supported by stabilizer platform 14 include, but are not limited to, reference transmitters (such as the reference transmitter 18 shown in FIG. 4), reference receivers, fiducials (such as the modular fiducials 20 shown in FIGS. 16-20), flexible arms (such as the flexible arm 22 shown in FIG. 13), rigid arms (such as the rigid arm 24 shown in FIG. 12), rotating arms, drill guides (such as the drill guide 60 shown in FIG. 15), drills (such as the drill 86 shown in FIG. 6), saws, reamers, other orthopedic instruments, other stabilizer platforms 14, support platforms (such as the support platforms 26a, b and c shown in FIGS. 9-11), monitoring devices, prosthetics or any other desired instrument or other item or structure. Instrument receivers such as apertures 30, slots 32, protrusions 34, instrument portals 50a, b, and c, or other suitable structures for capturing, securing and/or stabilizing items may be included at various locations on stabilizer platform 14. Consequently, items may be supported in various locations and orientations as is desired and/or convenient.

Reference transmitters 18, may be formed similarly and function similarly to typical reference transmitters 10 for use in tracking systems, such as the tracking systems described in the documents incorporated by reference into this document. However, reference transmitters 18, when captured and stabilized by a stabilizer platform 14, which is in turn secured to an individual's anatomy, may be more secure, stable and/or may be less likely to be dislodged and/or repositioned than typical reference transmitters 10 secured to an individual's anatomy in typical fashions. FIG. 4 shows a reference transmitter 18 captured by protrusions 34, securing the reference transmitter 18 to the platform 14.

Items may be captured by receivers, securing the items to the platform 14. Receivers may be apertures 30 extending through portions of stabilizer platform 14. Some of the other receivers shown in FIG. 4 are protrusions 34 extending through stabilizer platform 14 and slots 32 extending through portions of stabilizer platform 14. In other embodiments, receivers may be any desired structure capable of capturing or securing instruments or any other desired item. For instance, receivers may include locks, channels, clamps, receptors or any structure adapted to support instruments or any other desired item.

Stabilizer platform 14 may be biased against a portion of an individual's anatomy, such as the skin, by fasteners. Fasteners may be any suitable structure adapted to secure stabilizer platform 14 to a portion of an individual's anatomy, such as, but are not limited to, surgical pins, fixation pins 38, surgical screws, other screws, bolts, straps, bands, adjustable collars or clamps. In certain embodiments, such as the embodiment shown in FIG. 4, a number of fixation pins 38 are used as fasteners.

Fixation pins 38 may secure stabilizer platform 14 to any desired and/or suitable portion of an individual's anatomy, such as body tissue, soft tissue, muscles, tendons, ligaments, cartilage, bony anatomy or any other desired and/or suitable anatomy. In certain embodiments of the present invention, fixation pins are inserted into bony anatomy to rigidly secure stabilizer platform 14. For instance, in embodiments where modular fiducials 20 or reference transmitters 18 for use with tracking systems are to be secured to stabilizer platform 14, the stabilizer platform 14 may be rigidly secured to a portion of an individual's bony anatomy to reduce the chance that the attached reference structure or structures will move.

Fixation pins 38, as well as other appropriate fasteners, may be assisted by retainers of various kinds. Retainers may assist fasteners to bias stabilizer platform 14 against an individual's skin. Retainers may include, but are not limited to, wing nuts 42 (as shown in FIG. 4), nuts, connectors 44 (as shown in FIG. 8), spring-loaded connectors, threaded connectors, spring-loaded threaded connectors, clips, e-clips, d-clips, snap locks or any other suitable structure. In certain embodiments, wing nuts 42, connectors 44 or both are used to assist fixation pins 38 to rigidly secure the stabilizer platform 14.

However, retainers are not required. Friction and/or other forces present between fixation pins 38 and apertures 30 may be sufficient to secure stabilizer platform 14 to a desired item in a stable fashion.

FIG. 7 shows stabilizer platform 14 including a first platform surface 46 and a second platform surface 48. First and second platform surfaces 46 and 48 may be formed in any desired and suitable shape and located in any desired and suitable orientation. The stabilizer platform shown in FIGS. 7 and 8 is generally circular, first platform surface 46 is an upper convex surface and second platform surface 48 is a lower concave surface. However, stabilizer platform 14 may be any shape appropriate to the anatomy to be treated, such as rectangles, triangles, ovals, squares, three-dimensional shapes, or any other desired shape. The size and shape of stabilizer platform 14 as well as the curvature and orientation of first upper convex platform surface 46 and second lower concave surface 48 may be adapted such that stabilizer platform 14 may be placed flush against a desired portion of an individual's anatomy, such as the individual's skin, with a low profile. This reduces the chance that stabilizer platform 14, or items secured to it, will experience unintentional contact during surgical procedures. The low profile of the stabilizer platform 14 also stabilizes the platform.

In some embodiments, second platform surface 48 is adapted to contact an individual's skin at least at three points. In the embodiment shown in FIG. 4 the lower surface 48 of platform 14 is adapted to contact an individual's skin at numerous points, lending stability to the platforms 14. In a preferred embodiment, platform 14 is formed from a semi-rigid material, allowing a large number of points of the platform to contact an individual's skin and conforming the platform to the individual's skin to create an especially stable platform.

In other embodiments, stabilizer platform 14 may be mounted to a table. In these embodiments, stabilizer platform 14 may preferably support at least three modular fiducials. In these embodiments, the individual may be secured to the table in conventional fashions such that the individual does not move with respect to the table.

As shown in FIG. 7, apertures 30 extend from first surface 46 to second surface 48. Apertures 30 may be formed in any desired and/or suitable size or shape. For example, apertures 30 are shown as circular and adapted to receive commercially available fixation pins. In a particular embodiment, apertures 30 are approximately 6 millimeters in diameter such that the apertures 30 may accept fixation pins 38 having diameters of approximately 5 millimeters. In some embodiments where apertures 30 are larger than fixation pins 38, surgeons may be able to adjust the position and/or orientation of the fixation pin 38 with respect to features of the individual's anatomy. In other embodiments, apertures 30 are circular and are approximately 5 millimeters in diameter such that the apertures 30 may accept fixation pins 38 having diameters of approximately 5 millimeters for a tight, secure fit. Additionally, any desired and/or suitably sized fixation pin 38, or other fastener may be used. Also, any desired and/or suitable number of fasteners may be used. Generally, increasing the number of fasteners may increase the stability of platform 14.

Apertures 30 may be formed such that the axes of at least some of the apertures 30 are not parallel with respect to at least some of the other apertures 30. As shown in FIG. 7, in some embodiments, some or all of the apertures 30 may be formed such that lower ends of the apertures 92 converge towards each other with respect to the upper ends 94 of the apertures 30. In other embodiments, apertures 30 may have lower ends 92 of the apertures 30 that diverge from each other with respect to the upper ends 94 of the apertures 30. For instance, the apertures 30 can be oriented so that their axes are radii of the curve forming platform 14. In still other embodiments, apertures 30 may be formed in other orientations with respect to one another.

In embodiments where apertures 30 converge towards each other, fixation pins 38 may also converge towards one another when inserted through apertures 30. The convergence of fixation pins 38 may rigidly secure stabilizer platform 14 to a portion of an individual's anatomy, such as the bony anatomy, rigidly biasing the stabilizer platform 14 against the individual's skin. In other embodiments, similar stabilizing effects may be achieved with aperture 30 and fastener arrangements allowing at least some fasteners to be non-parallel with respect to one another.

Preferably, apertures 30 are of sufficient diameter to permit fixation pins 38, or any other desired fasteners, to be inserted through stabilizer platform 14 such that at least one of the fixation pins 38 is not parallel with respect to at least one other fixation pin 38. In some embodiments, apertures 30 are of sufficiently large diameter (or optionally fixation pins 38 are of sufficiently small diameter) to permit fixation pins 38 to converge at distal ends 96 relative to proximate ends 98 of fixation pins 38. Securing stabilizer platforms 14 in the manners described above may allow a surgeon to control the height of the stabilizer platform 14 relative to desired portions of the individual's anatomy.

In some embodiments, apertures 30 may be formed from structures extending from peripheral portions of stabilizer platform 14, rather than extending from first platform surface 46 to second platform surface 48.

Alternatively, stabilizer platform 14 may be formed without apertures 30. In this case, fasteners, such as surgical screws or other appropriate and/or desired fasteners are inserted through portions of stabilizer platform 14 into portions of an individual's anatomy or fasteners may be integral to stabilizer platform 14 and may extend downward from second platform surface 48. Integral fasteners may include prongs, barbs or other suitable structures. Stabilizer platform 14 with integral fasteners may be biased against an individual's anatomy by pressing or forcing stabilizer platform 14 onto a desired portion of an individual's anatomy. In some embodiments, integral fasteners are formed such that at least one of the integral fasteners is not parallel to at least one other integral fastener. For example, at least one of the integral fasteners may converge towards at least one other integral fastener.

In use, the stabilizer platform 14 may be placed proximate to a portion of the individual's anatomy such that at least three points of the second platform surface 48 contact the skin of the individual. A first fixation pin 38 is inserted through an aperture 30 extending through portions of stabilizer platform 14. Fixation pin 38 may be self-tapping and/or may require the surgeon to first incise and/or drill a pilot hole prior to insertion of fixation pin 38 into the desired portion of the individual's anatomy. Fixation pins 38 may be connected to bone in conventional manners. Next, at least one additional fixation pin 38 is inserted through stabilizer platform 14 into the desired portion of the individual's anatomy. In certain embodiments, fixation pins 38 converge towards one another at distal ends 96, such as is illustrated in FIG. 7. Additional fixation pins 38 may be inserted if desired to provide additional stability and/or rigidity. In embodiments where maximum stability and/or rigidity are desired, fixation pins 38 may be secured to bony anatomy, or other suitable structure. Retainers such as connectors 44 or wing nuts 42 may be secured to proximal ends of fixation pins 38. Finally, any desired item or items may be secured to the stabilizer platform 14. After the completion of the desired surgical procedures, stabilizer platform 14 may be removed from the individual's anatomy.

Figure 10:
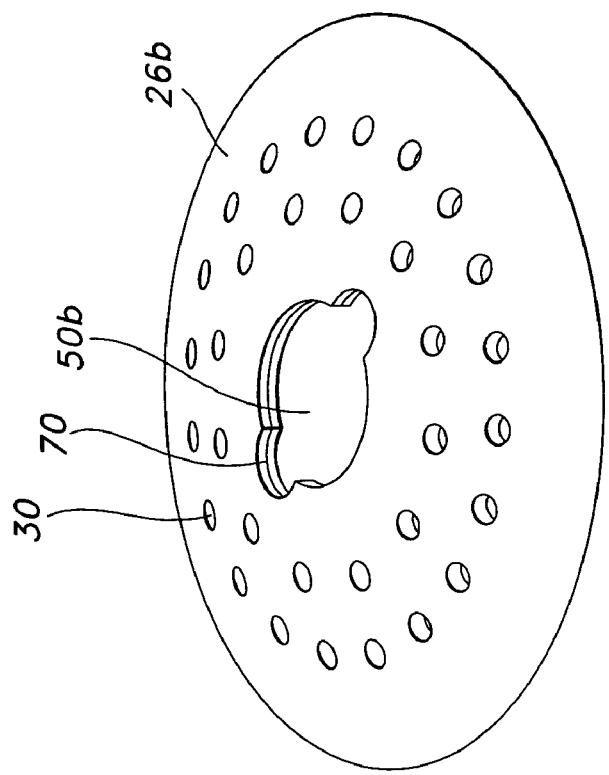
FIG. 10 shows a perspective view of a support platform according to another embodiment of the present invention.
Figure 9:
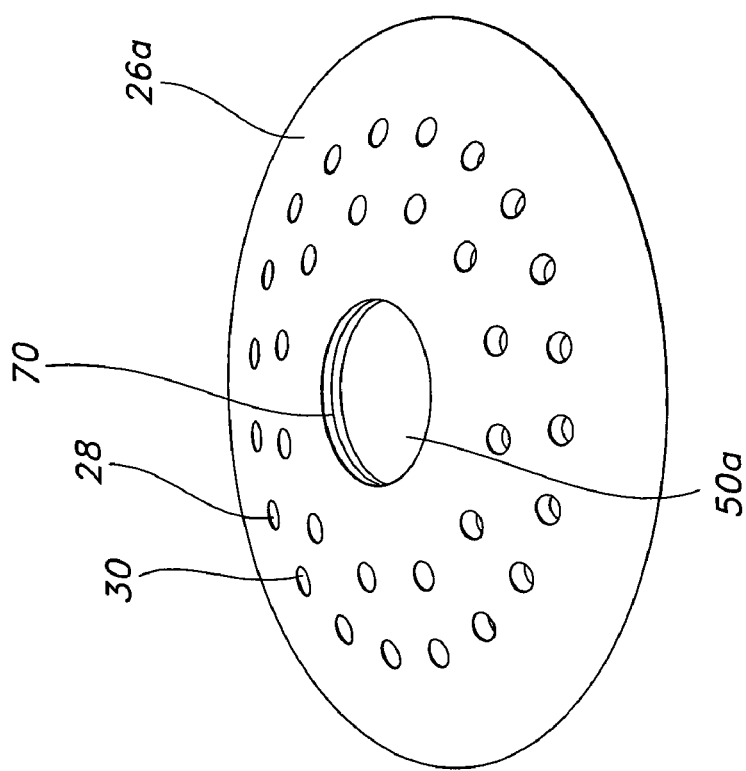
FIG. 9 shows a perspective view of a support platform according to another embodiment of the present invention.
Figure 11:
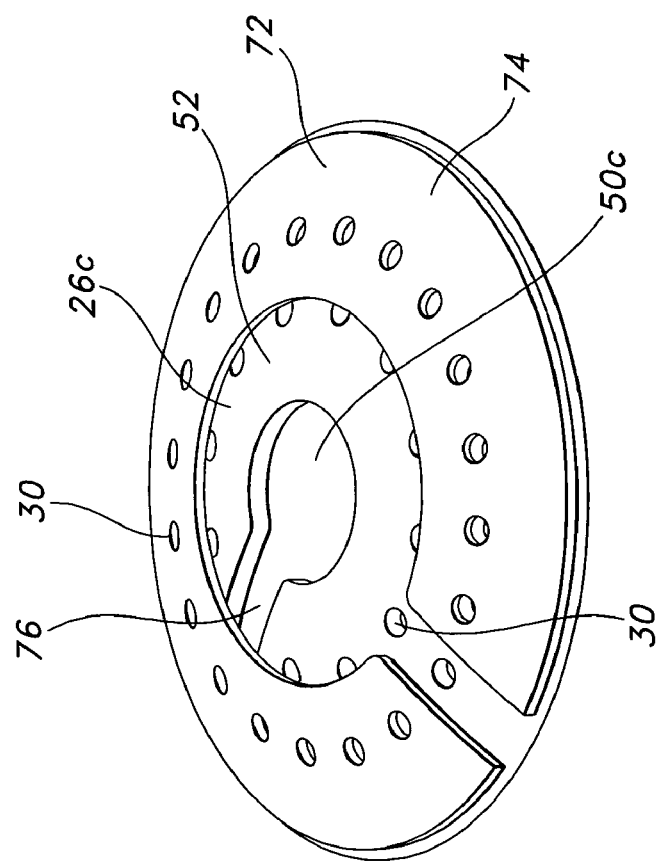
FIG. 11 shows a perspective view of a support platform according to another embodiment of the present invention.

FIGS. 9-11 show various support platforms 26a, b and c according to embodiments of the present invention. FIG. 9 shows a first embodiment of a support platform 26a, which may be shaped and sized similarly to stabilizer platform 14 and formed in a similar manner. However, the support platforms of this invention may be formed in any desired shape and size from any desired and/or appropriate material. Support platform 26a includes an instrument portal 50a adapted to receive an item. In some embodiments, support platform 26a may be secured to an individual in a similar or different manner as stabilizer platform 14.

Figure 3:
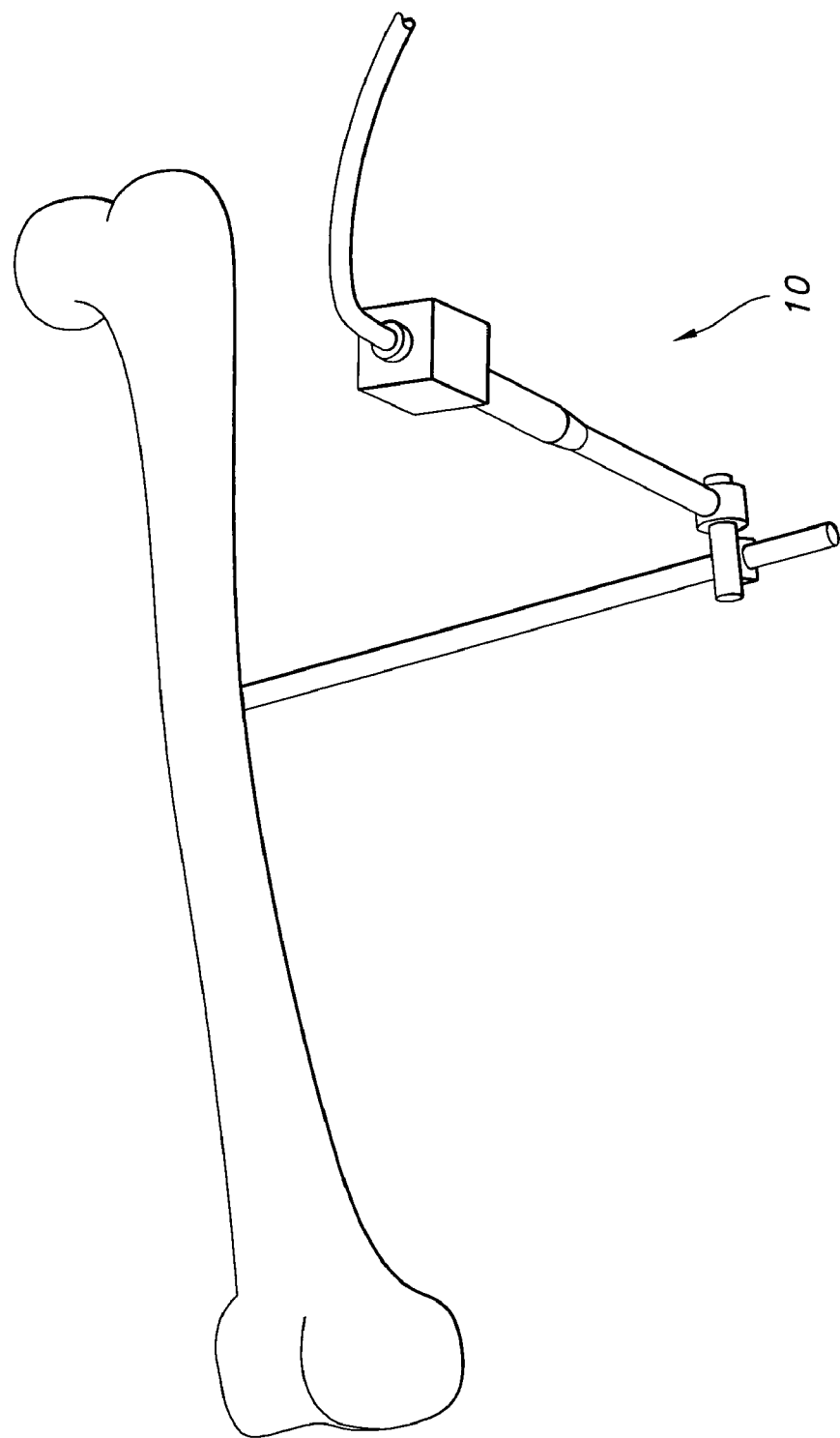
FIG. 3 shows a side view of a reference transmitter secured to a portion of bone.

Items may be supported in a rigid or moveable manner by various embodiments of support platforms 26a, 26b and/or 26c. Exemplary items include, but are not limited to: reference transmitters (such as the reference transmitter 18 shown in FIG. 3), reference receivers, modular fiducials (such as the modular fiducials 20 shown in FIGS. 16-20), active modular fiducials, passive modular fiducials, typical fiducials, typical reference structures, flexible arms (such as the flexible arm 22 shown in FIG. 13), rigid arms (such as the rigid arm 24 shown in FIG. 12), rotatable arms, fasteners, drill guides (such as the drill guide 60 shown in FIG. 15), drills (such as the drill 86 shown in FIG. 6), saws, reamers, other orthopedic instruments, other stabilizer platforms (such as the stabilizer platform 14 shown in FIG. 7), support platforms (such as the support platforms 26a, 26b and 26c shown in FIGS. 9-11), monitoring devices, prosthetics or any other desired instrument or other item. Items may be captured by support platforms 26a, 26b and 26c in ways similar to or the same as items are supported by stabilizer platform 14, for example, by receivers.

As shown in FIG. 9, receivers include a number of apertures 30 extending through portions of support platform 26a as well as an instrument portal 50a. Instrument portals may be sized and shaped as desired. For instance, FIGS. 9-11 show instrument portals 50a, 50b and 50c respectively. Item receivers may also be any other structures capable of securing an item, such as the structures on stabilizer platforms 14 discussed above.

Figure 15:
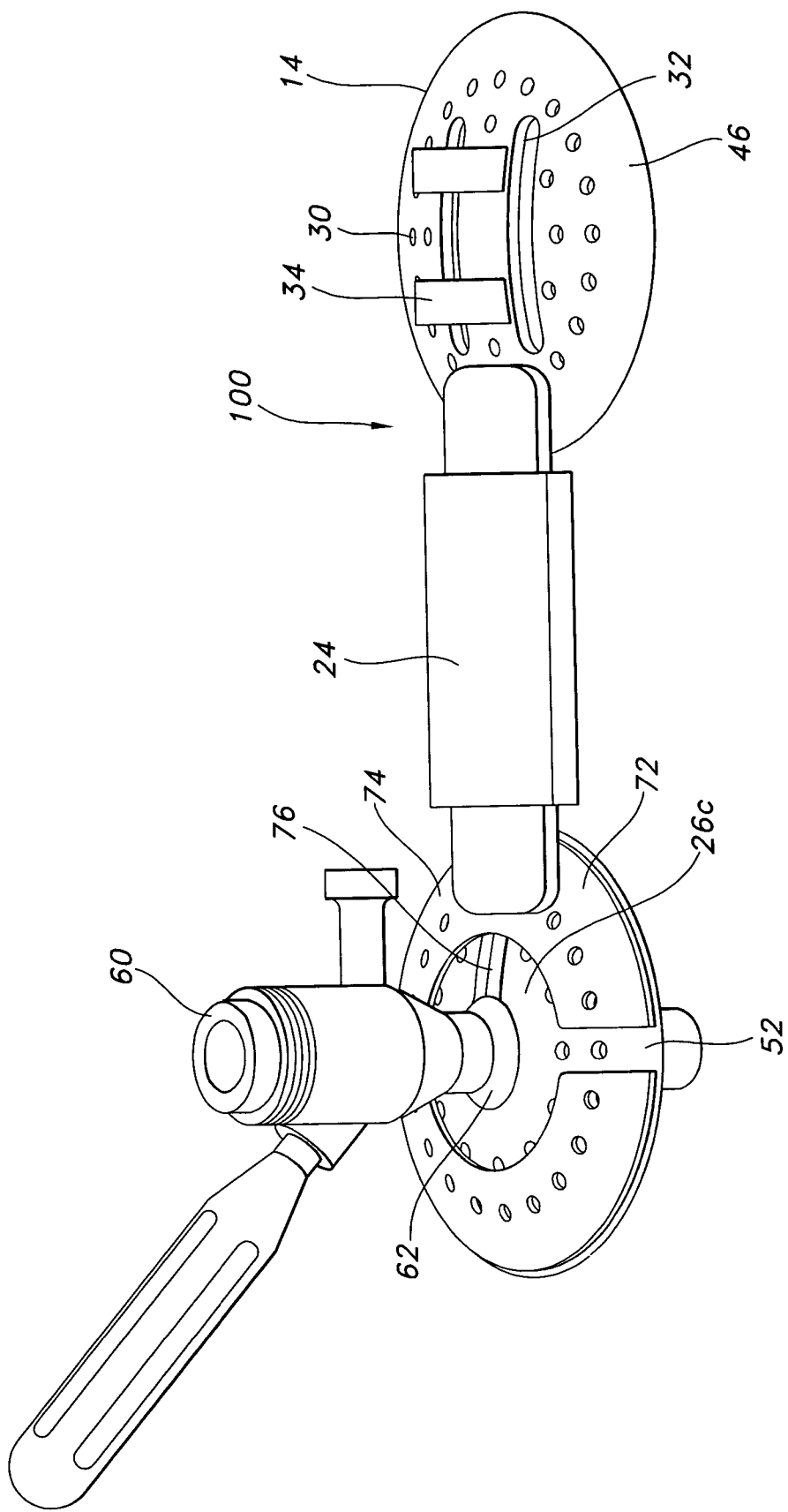
FIG. 15 shows a perspective view of a surgical instrument positioner according to another embodiment of the present invention.

FIG. 15 shows a support platform 26c attached to a stabilizing system 100, including a stabilizer platform 14 and a rigid arm 24, rather than being directly secured to an individual's anatomy. In this and other embodiments, support platforms 26a, 26b and/or 26c are not secured directly to a portion of an individual's anatomy, but instead, they are at least partially stabilized by an arm, such as the arms 22 and 24 shown in FIGS. 13 and 12 respectively. The arm 22 or 24 can be connected to a stabilizer platform 14, which is in turn rigidly or non-rigidly biased against a portion of an individual's anatomy. The arm 22 or 24 that stabilizes the support platform 26a, 26b or 26c may be secured to the support platform by any appropriate stabilizer receiver, such as apertures 30 or any other appropriate structure.

As shown in FIG. 15, stabilizer platform 14, in connection with an arm 22 or 24, or by itself, may serve as a stabilizing system 100 for a support platform 26c. Stabilizer system 100 may also be used in conjunction with support platforms 26a and 26b. Items associated with support platform 26a, 26b and/or 26c will be stabilized when support platform is connected to stabilizer platform 14 secured to a portion of an individual's anatomy. Use of such a stabilization system may aid a surgeon to precisely navigate, align and/or position items during orthopedic procedures or other general surgical procedures. A surgeon may connect as many support platforms to stabilizer platform 14 as is desired, obviating the need to use excessive amounts of fasteners in some procedures.

Figure 5:
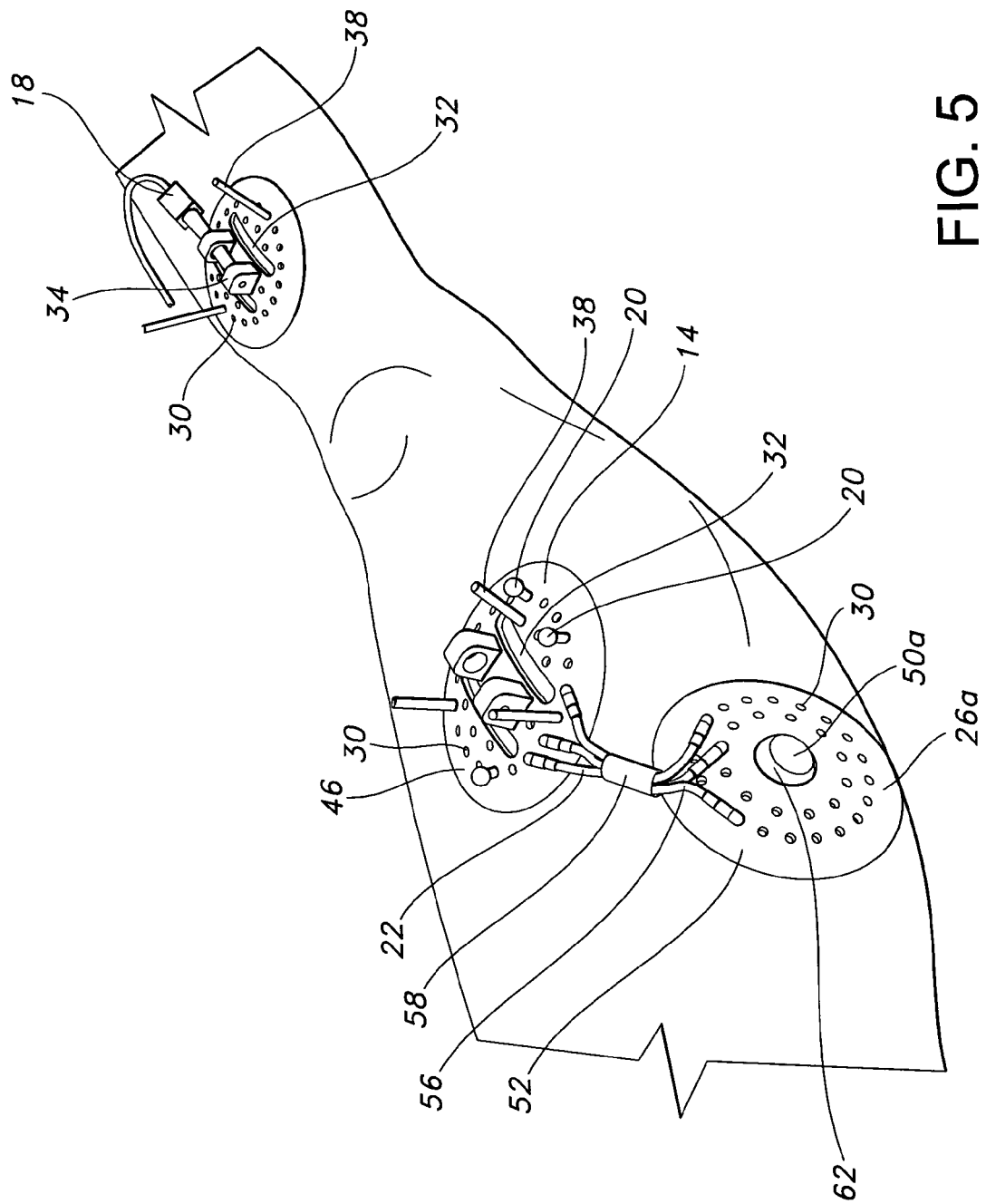
FIG. 5 shows a perspective view of a number of platforms according to another embodiment of the present invention, some of the platforms biased against an individual's skin and some of the platforms connected to some of the other platforms.
Figure 6:
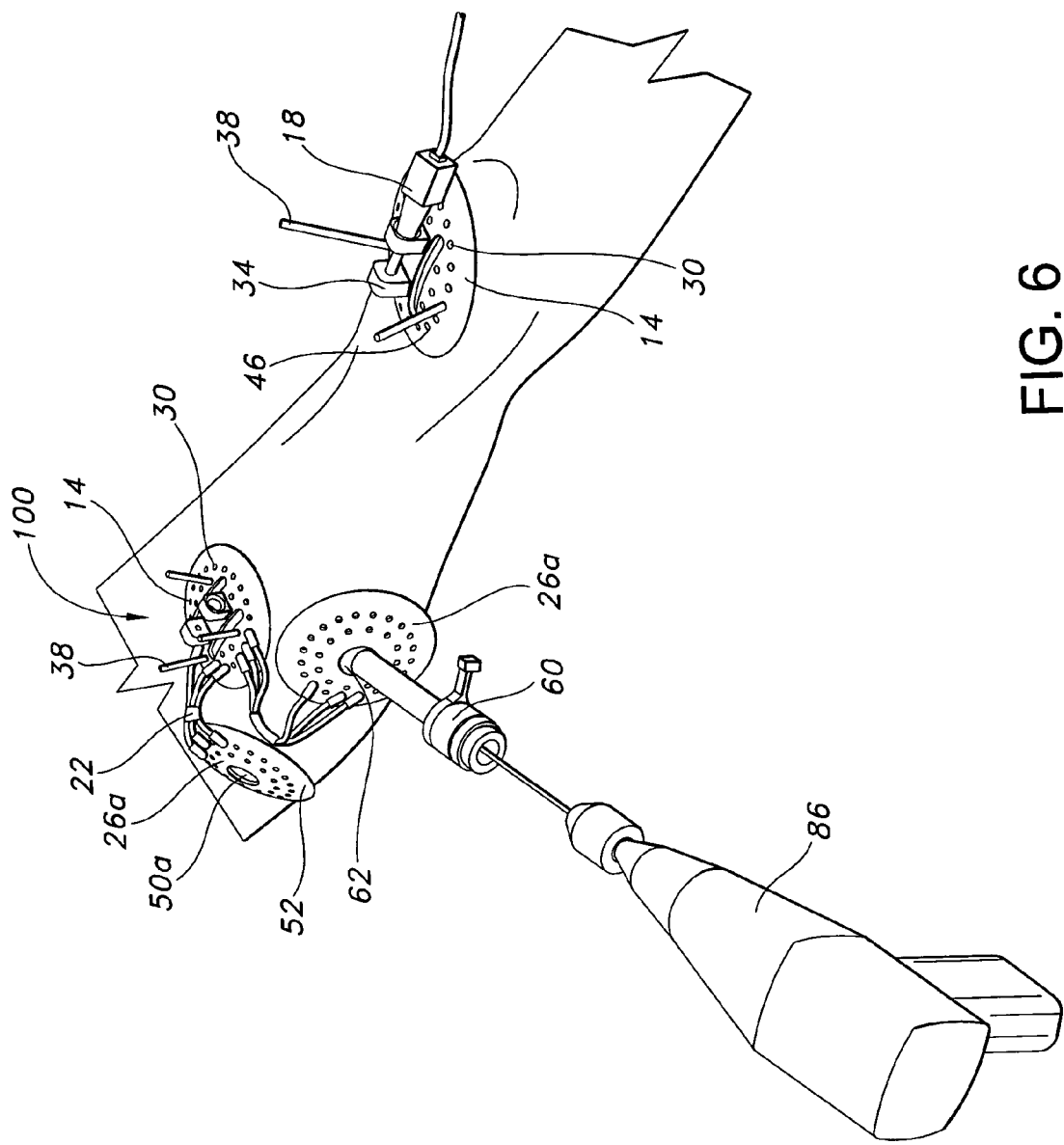
FIG. 6 shows a perspective view of a number of platforms according to another embodiment of the present invention, some of the platforms being used to guide and stabilize a surgical drill.
Figure 12:
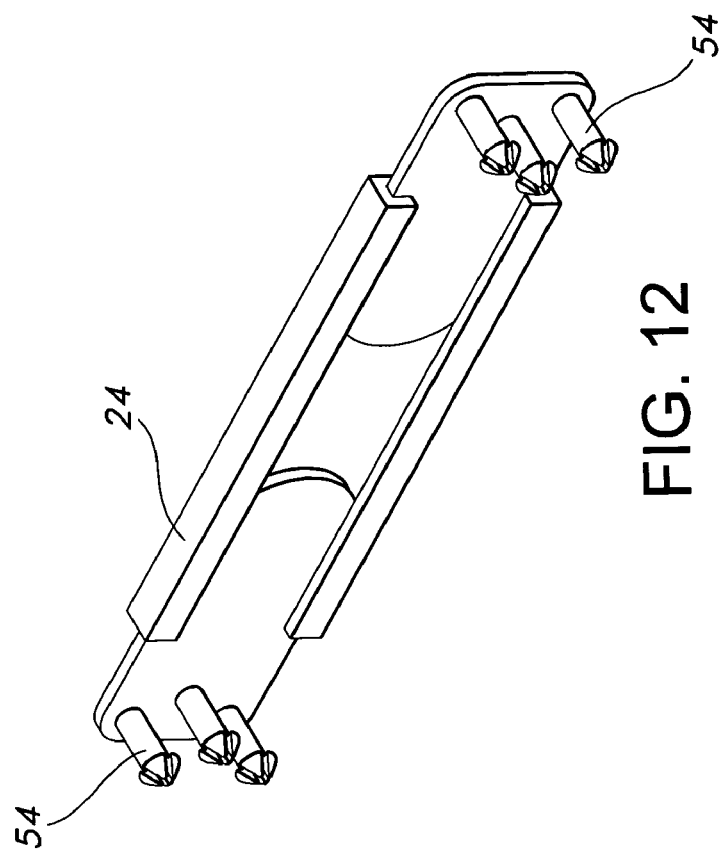
FIG. 12 shows a perspective view of a rigid arm useful in certain embodiments of the present invention.
Figure 13:
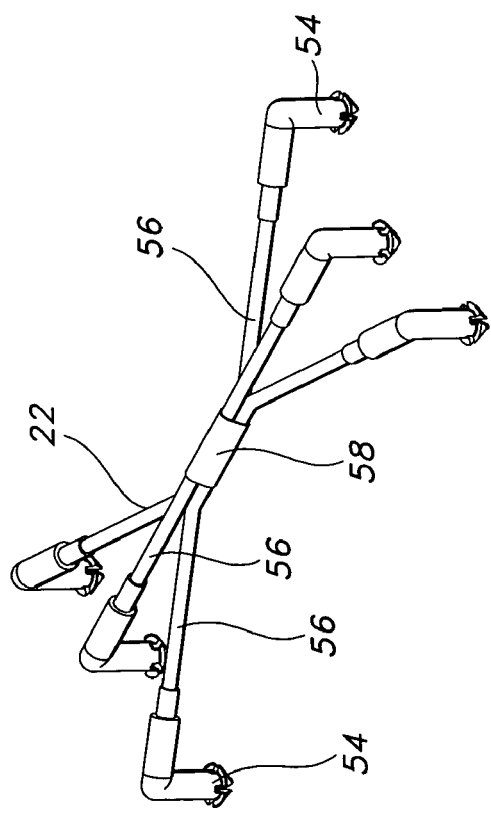
FIG. 13 shows a perspective view of a flexible arm useful in certain embodiments of the present invention.

FIGS. 12 and 13 show arms 24 and 22 respectively, for stabilizing and/or securing support platforms 26a, 26b and/or 26c with respect to stabilizer platform 14. Arms 22 and 24 may connect to stabilizer platform 14 and/or support platform 26a, 26b and/or 26c by optional snap pins 54 extending from portions of the arms 22 and/or 24. Optional snap pins 54 may be adapted to be inserted into stabilizer receivers such as apertures 30 on stabilizer platform 14 and/or support platforms 26a, 26b and 26c, securing the arm 22 or 24 to either the stabilizer platform 14 or the support platform. Any suitable mechanism may be used to secure arm 22 and/or 24 to the platforms according to various embodiments of the present invention. Alternatively, arm 22 and/or 24 may be integral with one or both of the platforms. As shown in FIGS. 5 and 6, arms 22 may be useful during surgical procedures for stabilizing platforms 26a while still allowing the platform 26a to be moved out of the way when not needed in order to allow the surgeon better visualization.

As shown in FIG. 12, rigid arm 24 may be extendable and retractable. However, rigid arm 24 does not have to be extendable or retractable. In some embodiments, rigid arm 24 may be adapted to rotate relative to stabilizer platform 14 and/or support platforms 26a, 26b and 26c. Use of rigid arm 24 may allow the surgeon to define an arc of a certain radius, useful in some surgical procedures.

FIG. 13 shows a flexible arm 22. Flexible arm 22 may be formed from a plurality of flexible bands 56 secured to one another by a collar 58. In some embodiments, one or more of the flexible bands 56 is formed from a material that is rigidly deformable and features sufficient memory to retain its shape once bent, under normal surgical use. These, or other, characteristics of flexible arm 22 may allow support platforms 26a, 26b or 26c to be positioned in a desired location relative to stabilizer platform 14, such as is shown in FIG. 5.

FIG. 15 shows a stabilizer platform 14 connected to a support platform 26c by a rigid arm 24. The support platform 26c is shown as stabilizing a drill guide 60. Drill guide 60 may be inserted through instrument portal 50c (shown in FIG. 11). In other embodiments, a working channel may be inserted through instrument portal 50c (or instrument portals 50a or 50b).

FIG. 15 shows drill guide 60 being supported and/or guided by bearing 62. Bearing 62 may be adapted to interact with the instrument portal at an outer surface 64 (shown in FIG. 14) in a sliding and/or rotating fashion. Bearing 62 may be adapted to capture or interact with instruments such as drill guide 60, at an inner surface 66 in a sliding and/or rotating fashion. Bearing 62 may similarly interact with instrument portal 50c (or instrument portals 50a or 50b) as well as instruments to allow the instruments to be repositioned with respect to support platform 26, yet still be stabilized by support platform 26a, 26b, or 26c. In other embodiments, bearing 62 may be adapted to guide the insertion of a surgical implant, such as a surgical nail.

Figure 14:
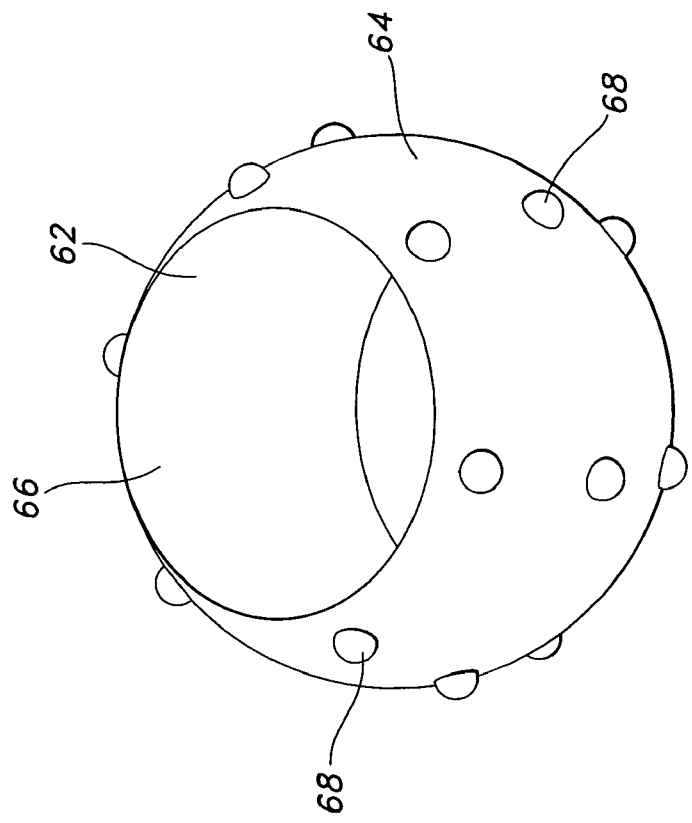
FIG. 14 shows a perspective view of a bearing useful in certain embodiments of the present invention.

In the embodiment shown in FIG. 14, bearing 62 includes a number of protrusions 68 extending from portions of the bearing outer surface 64. Protrusions 68 may be formed into any desired and/or suitable shape and dimension. Protrusions 68 may be adapted to interact with portions of portal 50a, b or c and/or upper and lower surfaces of a support platform such that bearing 62 remains in a desired orientation with respect to the support platform unless reoriented by a surgeon or other user. This feature assists surgeons or other users to properly align items during surgical and other procedures. In certain embodiments, at least one or more of the protrusions 68 may interact with a channel 70 at least partially circumscribing the interior of the instrument portal 50a (as shown in FIG. 9) to assist bearing 62 remaining in desired orientations. Bearing 62 may also be used with instrument portals 50b and 50c in support platforms 26b and 26c respectively.

Another embodiment of a support platform is shown in FIG. 11 as support platform 26c including a sliding ring 72. Sliding ring 72 may be formed from similar materials and in a similar manner as support platform 26c. Sliding ring 72 may be adapted to mount onto a surface on support platform 26c in a flush manner. As shown in FIG. 11, sliding ring 72 includes an upper convex surface 74 and a lower concave surface (not shown). The lower concave surface of sliding ring 72 is adapted to mount onto the first surface of the support platform 52c. Sliding ring 72 may include apertures 30 formed and shaped in a similar manner to apertures 30 of the support platforms 26a, 26b and 26c and stabilizer platforms 14. Sliding ring 72 may rotate with respect to support platform 26c to allow for fine-tuning of the positioning of items secured to apertures 30 of sliding ring 72.

As shown in FIG. 11, support platform 26c may define a gap 76. The gap 76 in the support platform 26c may extend from instrument portal 50c to an edge of support platform 26c. The gap 76 is adapted to allow the support platform 26c to be removed from items, such as a drill guide 60, during a surgical procedure without requiring removal of the items from the individual's anatomy. A gap may also be formed in sliding ring 72.

In use, stabilizer platform 14 is secured to a portion of an individual's anatomy as described above, proximate an area where the surgeon desires to use an item stabilized and/or guided by support platform 26a, 26b or 26c. One end of flexible arm 22 may be secured to support platform 26a, 26b or 26c by inserting snap pins 54 into apertures 30, and the other end of flexible arm 22 may be secured to stabilizer platform 14 in a similar manner. Support platform 26a, 26b or 26c is then positioned over the desired portion of the individual's anatomy. The desired items may then be inserted through instrument portal 50a, 50b or 50c, or otherwise supported by support platform 26, to allow items such as a drill guide 60 including a bearing 62 with protrusions 68, to be stabilized and/or guided during instrument navigation.

Various aspects and embodiments of the present invention include fiducial structures, such as the modular fiducials 20 shown in FIGS. 16-20. Modular fiducials 20 may be arranged securely on an item to form a pattern, the pattern (and consequently the item the pattern is secured to) capable of being tracked by a tracking system, such as the systems described above. Modular fiducials 20, unlike other reference structures that include three fixed fiducials, may be positioned independently of each other. As shown in FIGS. 16-20, modular fiducials 20 may include reflective elements 78 which may be tracked by a number of sensors whose output may be processed in concert by associated processing functionality to geometrically calculate the position and orientation of the item to which the modular fiducial 20 is attached. The modular fiducials 20 and the sensors need not be confined to the infrared spectrum. Any electromagnetic, electrostatic, light, sound, radio frequency or other desired technique may be used. Alternatively, modular fiducials 20 may "actively" transmit reference information to a tracking system, as opposed to "passively" reflecting infrared or other forms of energy.

Figure 17:
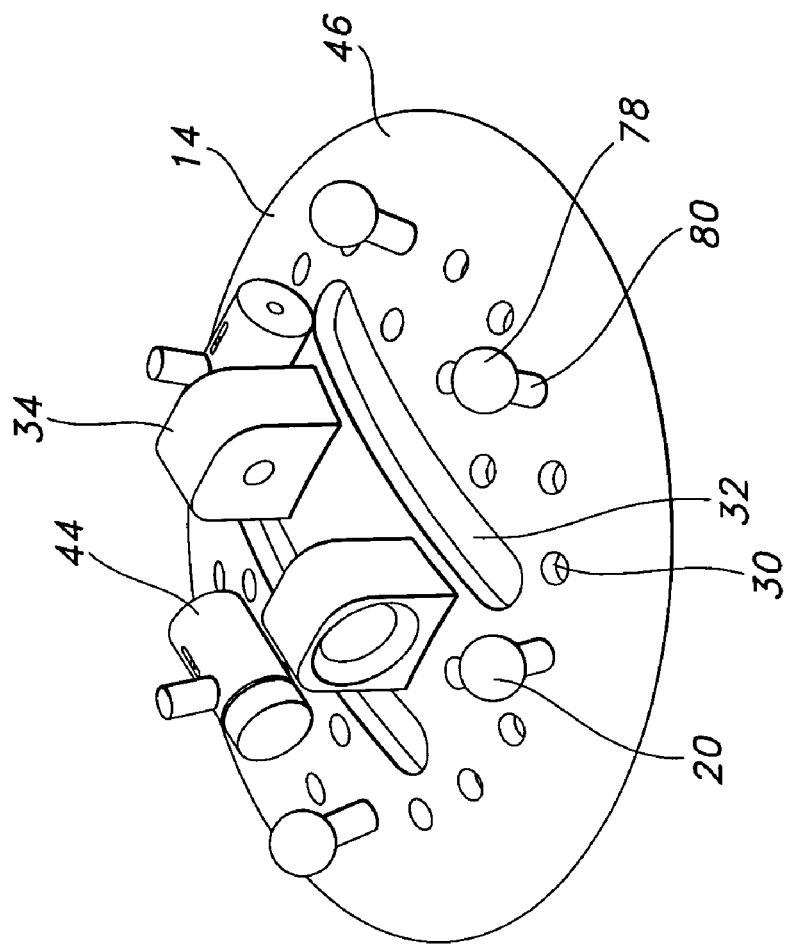
FIG. 17 shows a perspective view of a stabilizer platform including a number of the modular fiducials of FIG. 16 according to another embodiment of the present invention.

In certain embodiments, the pattern formed by the modular fiducials 20 is one that the tracking system is capable of accurately tracking as the item changes in location and/or orientation. Modular fiducials 20 may be arranged in any pattern as long as the tracking system is able to discern the precise location of the item by tracking the fiducials. FIG. 17 shows an exemplary pattern formed by modular fiducials 20 inserted into apertures 30 on stabilizer platform 14. The pattern formed by modular fiducials 20 allows the tracking system to recognize the position and orientation of the pattern in three dimensions. In other words, as the platform changes position and/or orientation, the tracking system "sees" the pattern and can accurately track the items location and orientation precisely. In some embodiments, modular fiducials 20 that are asymmetrically arranged with respect to one another will form suitable patterns.

Various techniques and methods may be followed to arrange modular fiducials 20 into suitable patterns. Because many patterns will result in suitable and/or acceptable patterns, surgeons may choose to locate modular fiducials 20 in convenient locations and then confirm that the tracking system is properly tracking the changes in position and orientation. Additionally, in some embodiments the tracking system may include a confirmation program that provides feedback to the surgeon, confirming that the modular fiducials 20 form an acceptable pattern and/or recommending alternative patterns that do form acceptable patterns if the surgeon's chosen pattern is inappropriate. In other embodiments templates may be used, including holes or other indications defining acceptable patterns. In some embodiments where modular fiducials 20 are to be used with the various platforms described in this application and/or surgical instruments, apertures 30 or other structures may be pre-marked, color-coded, indexed or otherwise identified indicating acceptable modular fiducial 20 placement.

In some embodiments, the pattern formed by modular fiducials 20 may be correlated with the orientation and position of the referenced item that the modular fiducials 20 are secured to by obtaining fluoroscopy images of the individual's anatomy at the same time the tracking system is tracking the pattern. In other embodiments, a probe bearing a suitable reference structure, the location and orientation of that reference structure already registered with the tracking system, may be used to register the location and orientation of the pattern and corresponding referenced item.

Modular fiducials 20 may be placed in locations to optimize the visibility of the modular fiducials 20 by the sensors of the tracking system. For instance, modular fiducials 20 may be located such that instruments, stabilizer platforms, support platforms, arms, wires, tubes, hoses, monitoring equipment, other equipment, portions of individuals (including the patient) or any other item do not obstruct the sensors "view" of the modular fiducials 20. Modular fiducials 20 may also be located in areas where they will be less likely to be accidentally contacted, repositioned or dislodged.

Figure 16:
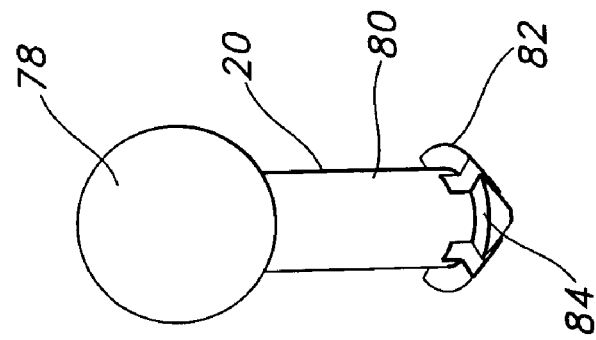
FIG. 16 shows a perspective view of a modular fiducial according to another embodiment of the present invention.
Figure 20:
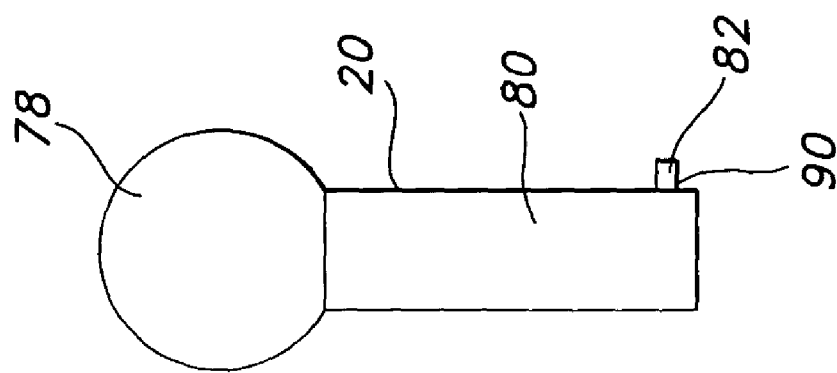
FIG. 20 shows a schematic side view of a modular fiducial according to another embodiment of the present invention.
Figure 19:
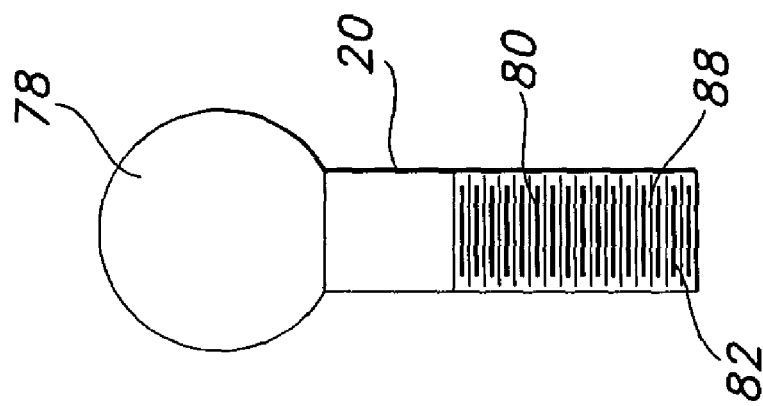
FIG. 19 shows a schematic side view of a modular fiducial according to another embodiment of the present invention.
Figure 18:
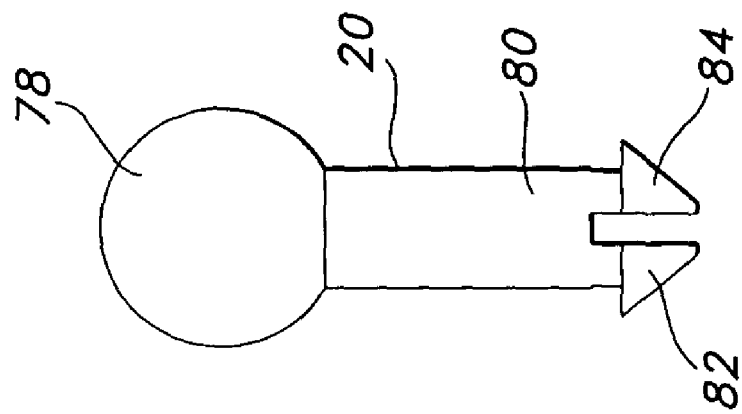
FIG. 18 shows a schematic side view of the modular fiducial of FIG. 16.

As shown in FIG. 17, modular fiducials 20 may be low profile in design, reducing the likelihood that they will be accidentally contacted, repositioned or dislodged. FIG. 16 shows a modular fiducial 20 that includes a reflective element 78, a stem 80, and a fastener 82. Fastener 82 is shown having a number of resilient arms 84 that permit modular fiducial 20 to be secured into apertures 30 of the various platforms described in this application, apertures located on an instrument or other item or into any other suitable and/or desired item. Resilient arms 84 may also permit modular fiducial 20 to be easily removed from one location and repositioned in another location if desired and/or needed. Fasteners 82 may also be formed as threads 88 (as shown in FIG. 19), bayonet pins 90 (as shown in FIG. 20), ball detents or any other suitable structure for securing modular fiducial 20 into apertures 30 or other locations.

Figure 1:
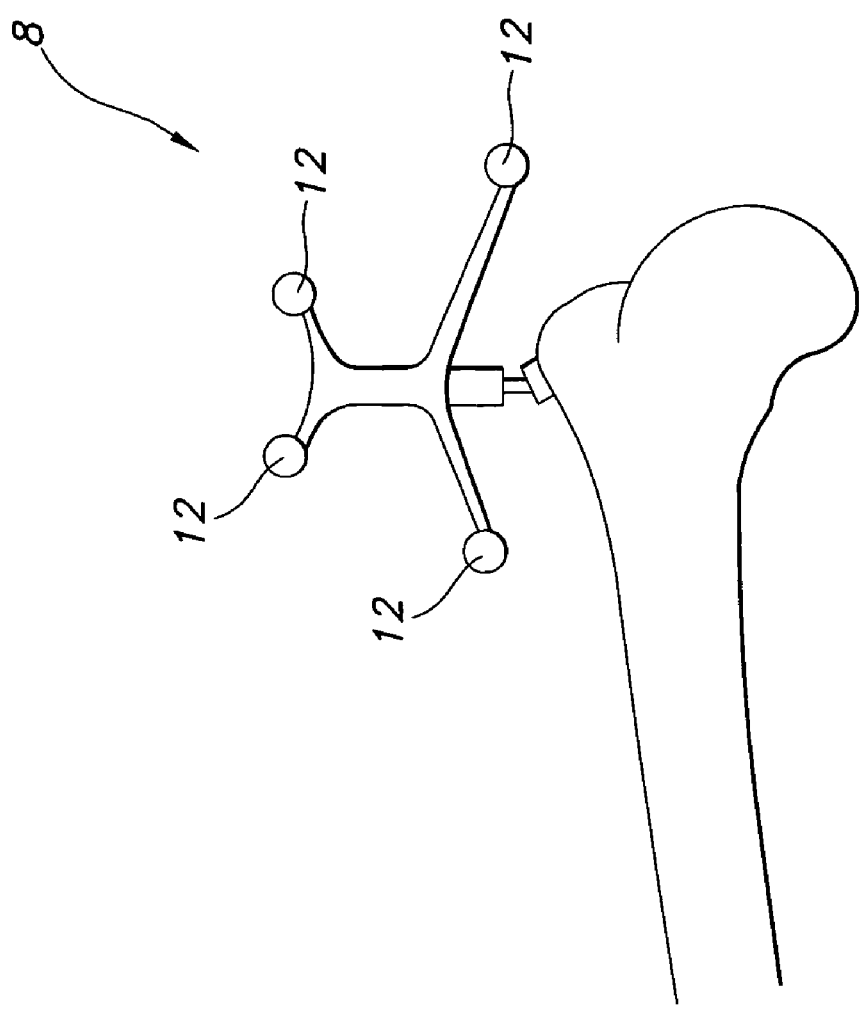
FIG. 1 shows a side view of a reference structure secured to a portion of bone.
Figure 2:
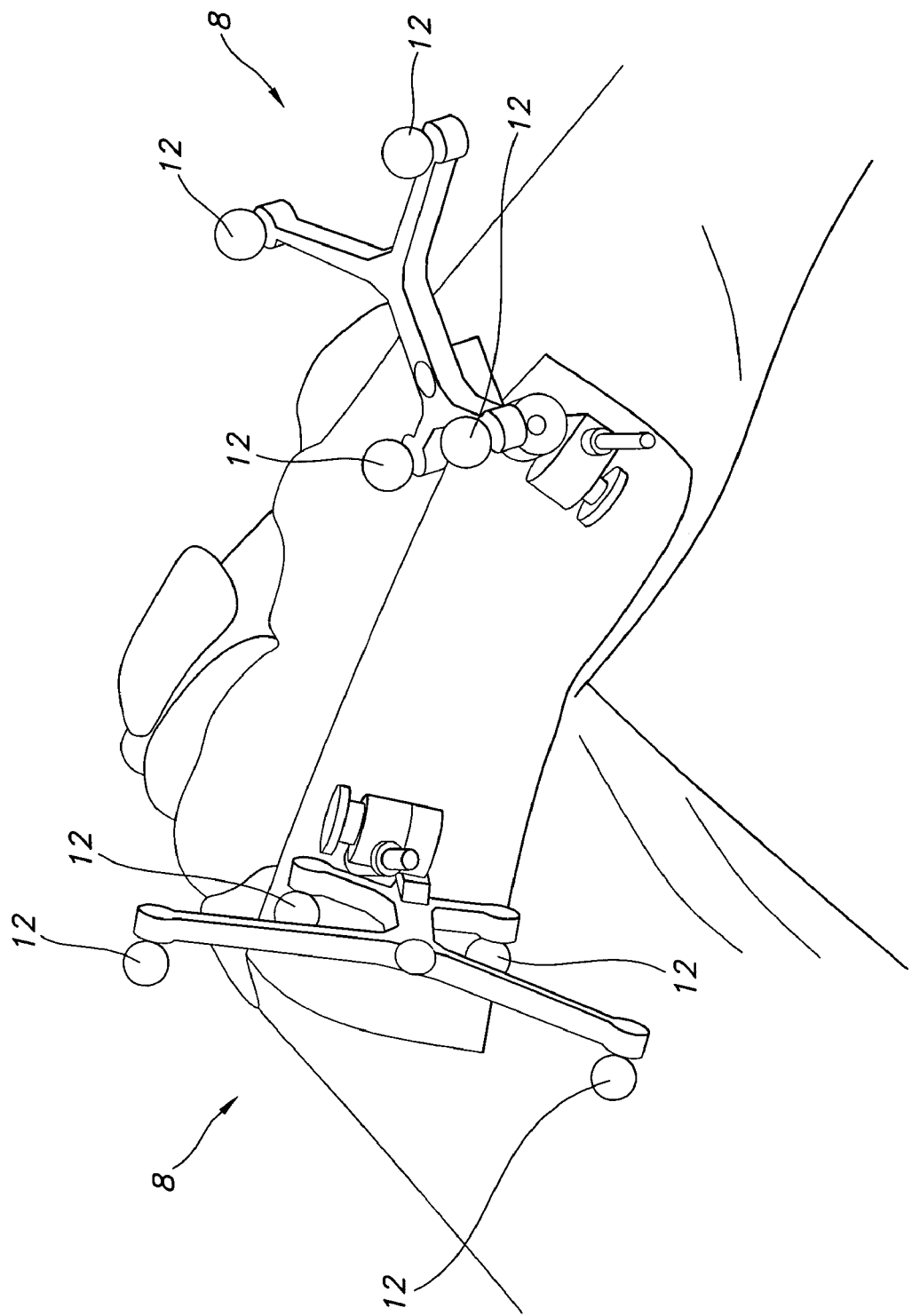
FIG. 2 shows a side view of two reference structures secured to portions of an individual's leg.

In alternative embodiments, fastener 82 may be adapted to secure the modular fiducial 20 directly to a portion of an individual's anatomy or instruments to be referenced. For instance, fastener 82 may be a pin, a fixation pin, a screw, a nail, a brad, a staple, a strap or any other suitable structure for securely fixing modular fiducial 20. By way of example, modular fiducials 20 may be rigidly secured to the femur and the tibia, in effect turning each the femur and tibia into reference structures. In some embodiments, securing the modular fiducials 20 directly to the item to be referenced in this manner may improve the accuracy of the tracking system because modular fiducials 20, in comparison to the typical reference structures 8 shown in FIGS. 1 and 2, may be spaced apart further. Consequently, small changes in orientation and/or positioning of the item to be referenced will have a greater effect in how the pattern "looks" with the modular fiducials 20 as opposed to typical reference structures 8. In other words, because modular fiducials 20 may be spaced farther apart than typical fiducials 12, changes in orientation and/or position of a referenced item will have a greater effect on the pattern created by the modular fiducials 20 than the pattern created by typical fiducials 12 secured to a typical reference structure 8.

In still other embodiments, modular fiducial 20 may be secured with adhesive, which may or may not be a permanent adhesive. In still other embodiments, stems 80 and fasteners 82 are not necessary to modular fiducial 20. Rather, reflective element 78 may be fixed directly to a surface to be referenced. In some embodiments, instruments may be formed with integral reflective elements 78, with or without stems, in suitable locations to allow the instruments to be tracked by a corresponding tracking system.

In certain methods of use, once a stabilizer platform 14 has been secured to a desired portion of an individual's anatomy, at least three or more, modular fiducials 20 are snapped into identified and/or appropriate apertures 30 located on stabilizer platform 14. The pattern formed by modular fiducials 20 is registered in the tracking system by an appropriate method, for instance, by the use of a C-arm to obtain fluoroscopy images and/or by the use of a registration probe. The position and orientation of the desired portion of the individual's anatomy can be tracked in real time. The platform may or may not be associated with other platforms or instruments.

This method can be modified as needed. For instance, if modular fiducials 20 are located on instruments on which the tracking system already has wire frame data or the like, no fluoroscopy images would need to be obtained. Rather, a registration probe could simply be used to enter the modular fiducials 20 pattern into the tracking system.

Figure 21:
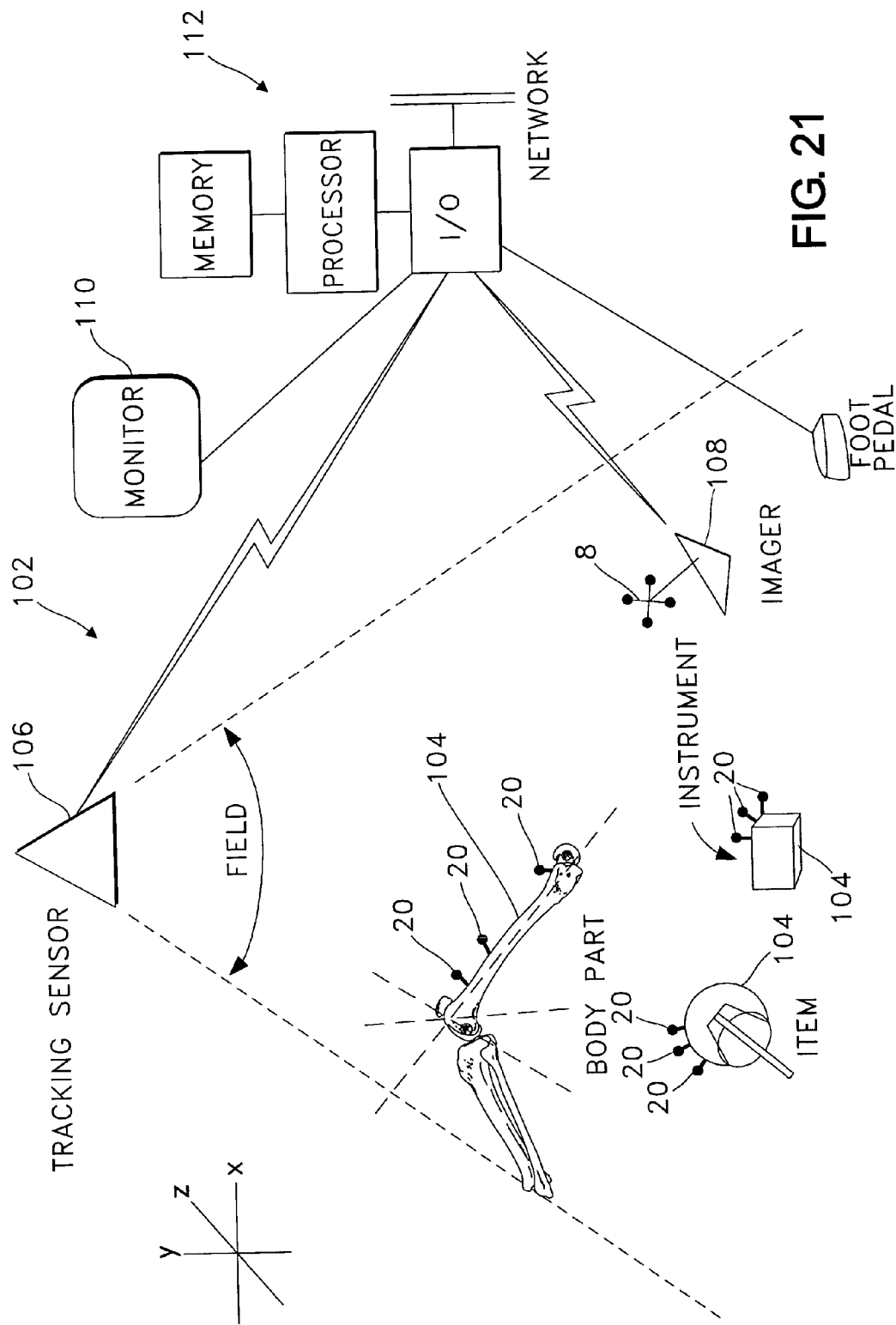
FIG. 21 shows a schematic view of a tracking system according to another embodiment of the present invention.

FIG. 21 shows a tracking system 102 that may utilize modular fiducials 20 to track the orientation and/or position of desired items 104 within the tracking sensor's 106 field of vision. Modular fiducials 20 or typical reference structures 8 may be placed on items 104 to be tracked such that a tracking system 102 can track the position and/or orientation of any desired item in the field of view of the tracking sensor 104. The tracking sensor 104 may relay the position and/or orientation data to a processing functionality 112 which can correlate the data with data obtained from an imaging device 108 and output that data to a suitable output device 110.

Changes and modifications, additions and deletions may be made to the structures recited above and shown in the drawings without departing from the scope or spirit of the invention.

What is claimed is:

1. A method for performing a surgical procedure on a patient comprising:
   (a) providing a platform that includes:
      (i) a concave surface and a convex surface, wherein the concave surface is configured to be biased against a portion of the patient's anatomy such that at least three points of the concave surface contact the portion of the patient's anatomy;
      (ii) at least two fasteners configured to secure the platform to the portion of the patient's anatomy, wherein each of the fasteners is configured to be connected to bone of the individual such that at least one of the fasteners is not parallel to at least one other of the fasteners;
      (iii) a plurality of receptacles that extend between the concave and convex surfaces of the platform, the receptacles configured to receive the fasteners in a plurality of angulations whereby the fasteners are configured to be oriented and positioned to fasten the platform to the portion of the patient's anatomy; and
      (iv) at least one portal structure extending from the convex surface of the platform, the portal structure including a guiding structure, the guiding structure configured to guide and orient a surgical item in a desired angular relationship with the portion of the patient's anatomy;

(b) securing the platform to the portion of the patient's anatomy using the fasteners;

(c) guiding the surgical item using the guiding structure; and (d) completing the surgical procedure.

2. The method of claim 1, wherein the guiding structure is a cylindrical bore.

3. The method of claim 2, wherein the bore extends in a direction radially from the concave surface.

4. The method of claim 1, wherein the at least one portal structure has a slot.

5. The method of claim 1, wherein the at least one portal structure is configured to receive a drill guide.

6. The method of claim 1, wherein the at least one portal structure is configured to receive a portion of a drill.

7. The method of claim 1, wherein the at least one portal structure is configured to receive a reamer.

8. The method of claim 1, wherein the at least one portal structure is configured to receive a saw.

9. The method of claim 1, wherein the platform further comprises a flexible arm configured to be affixed to the portion of the patient's anatomy.

10. The method of claim 1, wherein the flexible arm is formed from a material with memory to retain its shape once bent.

11. The method of claim 1, wherein the platform further comprises a plurality of protrusions, wherein at least some of the protrusions are configured to interact with the surgical item in a rotating or sliding fashion.

12. A method for performing a surgical procedure on a patient comprising:

(a) providing a platform that includes:
   (i) a concave surface and a convex surface, wherein the concave surface is configured to be biased against a portion of the patient's anatomy such that at least three points of the concave surface contact the portion of the patient's anatomy;
   (ii) a flexible arm configured to secure the platform to the portion of the patient's anatomy;
   (iii) at least one portal structure extending from the convex surface of the platform, the portal structure including a guiding structure, the guiding structure configured to guide and orient a portion of a drill in a desired angular relationship with the portion of the patient's anatomy; and
   (iv) a plurality of protrusions, wherein at least some of the protrusions are configured to interact with the portion of the drill in a rotating or sliding fashion;

(b) securing the platform to the portion of the patient's anatomy using the flexible arm;

(c) guiding the portion of the drill using the guiding structure; and (d) completing the surgical procedure.

13. The method of claim 12, wherein the guiding structure is a cylindrical bore.

14. The method of claim 13, wherein the bore extends in a direction radially from the concave surface.

15. The method of claim 12, wherein the at least one portal structure is configured to receive a drill guide.

16. The method of claim 12, wherein the at least one portal structure has a slot.

17. The method of claim 16, wherein the at least one portal structure is configured to receive a saw.

18. A method for performing a surgical procedure on a patient comprising:

(a) providing a platform that includes:
   (i) a concave surface and a convex surface, wherein the concave surface is configured to be biased against a portion of the patient's anatomy such that at least three points of the concave surface contact the portion of the patient's anatomy;
   (ii) a flexible arm configured to secure the platform to the portion of the patient's anatomy; and
   (iii) at least one portal structure extending from the convex surface of the platform, the portal structure including a guiding structure, the guiding structure configured to guide and orient a portion of a surgical item in a desired angular relationship with the portion of the patient's anatomy;

(b) securing the platform to the portion of the patient's anatomy using the flexible arm;

(c) guiding the surgical item using the guiding structure; and (d) completing the surgical procedure.

19. The method of claim 18, wherein the guiding structure is a cylindrical bore.

20. The method of claim 19, wherein the bore extends in a direction radially from the concave surface.

21. The method of claim 18, wherein the at least one portal structure has a slot.

22. The method of claim 18, wherein the at least one portal structure is configured to receive a drill guide.

23. The method of claim 18, wherein the at least one portal structure is configured to receive a portion of a drill.

24. The method of claim 18, wherein the at least one portal structure is configured to receive a reamer.

25. The method of claim 18, wherein the at least one portal structure is configured to receive a saw.

26. The method of claim 18, wherein the platform further comprises a plurality of protrusions, wherein at least some of the protrusions are configured to interact with the surgical item in a rotating or sliding fashion.

27. A method for performing a surgical procedure on a patient comprising:

(a) providing a platform that includes:
   (i) a concave surface and a convex surface, wherein the concave surface is configured to be biased against a portion of the patient's anatomy such that at least three points of the concave surface contact the portion of the patient's anatomy;
   (ii) at least two fasteners configured to secure the platform to the portion of the patient's anatomy, wherein each of the fasteners is configured to be connected to bone of the individual such that at least one of the fasteners is not parallel to at least one other of the fasteners;
   (iii) a plurality of receptacles that extend between the concave and convex surfaces of the platform, the receptacles configured to receive the fasteners in a plurality of angulations whereby the fasteners are configured to be oriented and positioned to fasten the platform to the portion of the patient's anatomy;
   (iv) a rigid arm configured to be affixed to the portion of the patient's anatomy;
   (v) at least one portal structure extending from the convex surface of the platform, the portal structure including a guiding structure, the guiding structure configured to guide and orient a surgical item in a desired angular relationship with the portion of the patient's anatomy; and (vi) a plurality of protrusions, wherein at least some of the protrusions are configured to interact with the portion of the drill in a rotating or sliding fashion;

(b) securing the platform to the portion of the patient's anatomy using the fasteners;

(c) affixing the rigid arm to the portion of the patient's anatomy;

(d) guiding the surgical item using the guiding structure; and (e) completing the surgical procedure.

28. The method of claim 27, wherein the guiding structure is a cylindrical bore.

29. The method of claim 28, wherein the bore extends in a direction radially from the concave surface.

30. The method of claim 27, wherein the at least one portal structure has a slot.

31. The method of claim 27, wherein the at least one portal structure is configured to receive a drill guide.

32. The method of claim 27, wherein the at least one portal structure is configured to receive a portion of a drill.

33. The method of claim 27, wherein the at least one portal structure is configured to receive a reamer.

34. The method of claim 27, wherein the at least one portal structure is configured to receive a saw.

* * * * *